United States Patent
Ding et al.

(10) Patent No.: US 10,258,613 B2
(45) Date of Patent: Apr. 16, 2019

(54) COMPOSITIONS FOR TREATING RETINAL DEGENERATION AND METHODS OF PRODUCTION AND USE THEREOF

(71) Applicant: The Board of Regents of the University of Oklahoma, Norman, OK (US)

(72) Inventors: Xi-Qin Ding, Edmond, OK (US); Hongwei Ma, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 3 days.

(21) Appl. No.: 15/115,819

(22) PCT Filed: Feb. 5, 2015

(86) PCT No.: PCT/US2015/014555
§ 371 (c)(1),
(2) Date: Aug. 1, 2016

(87) PCT Pub. No.: WO2015/120115
PCT Pub. Date: Aug. 13, 2015

(65) Prior Publication Data
US 2017/0007589 A1 Jan. 12, 2017

Related U.S. Application Data

(60) Provisional application No. 61/935,919, filed on Feb. 5, 2014.

(51) Int. Cl.
| | |
|---|---|
| *A61K 31/085* | (2006.01) |
| *A61K 31/19* | (2006.01) |
| *A61K 31/451* | (2006.01) |
| *A61K 31/09* | (2006.01) |
| *A61K 31/16* | (2006.01) |
| *A61K 31/4409* | (2006.01) |
| *A61K 31/17* | (2006.01) |
| *A61K 31/341* | (2006.01) |
| *A61K 31/35* | (2006.01) |
| *A61K 31/4412* | (2006.01) |
| *A61K 31/473* | (2006.01) |
| *A61K 31/495* | (2006.01) |
| *A61K 9/00* | (2006.01) |
| *A61K 31/192* | (2006.01) |

(52) U.S. Cl.
CPC .......... *A61K 31/451* (2013.01); *A61K 9/0048* (2013.01); *A61K 31/085* (2013.01); *A61K 31/09* (2013.01); *A61K 31/16* (2013.01); *A61K 31/17* (2013.01); *A61K 31/192* (2013.01); *A61K 31/341* (2013.01); *A61K 31/35* (2013.01); *A61K 31/4409* (2013.01); *A61K 31/4412* (2013.01); *A61K 31/473* (2013.01); *A61K 31/495* (2013.01)

(58) Field of Classification Search
CPC .................................................... A61K 31/085
See application file for complete search history.

(56) References Cited

U.S. PATENT DOCUMENTS

| 6,054,485 A | 4/2000 | Schwartz et al. |
| 2006/0292203 A1 | 12/2006 | Dellamary et al. |
| 2009/0022806 A1 | 1/2009 | Mousa et al. |

OTHER PUBLICATIONS

Koehler, "Thyroid Receptor Ligands. 6. A High Affinity "Direct Antagonist" Selective for the Thyroid Hormone Receptor", J. Med. Chem. 2006, 49, 6635-6637.*

Hwang, et al.; "Methylsulfonylnitrobenzoates, a New Class of Irreversible Inhibitors of the Interaction of the Thyroid Hormone Receptor and Its Obligate Coactivators That Functionally Antagonizes Thyroid Hormone," The Journal of Biological Chemistry, (2011), vol. 286, No. 14, pp. 11895-11908.

Scheppke, et al.; "Retinal Vascular Permeability Suppression by Topical Application of a Novel VEGFR2/Src Kinase Inibitor in Mice and Rabbits," The Journal of Clinical Investigation, (2008), vol. 118, No. 6, pp. 2337-2346.

Nguyen, et al.; "Hammett Analysis of Selective Thyroid Hormone Receptor Modulators Reveals Structural and Electronic Requirements for Hormone Antagonists," J. Am. Chem. Soc. (2005), vol. 127, pp. 4599-4608.

Baxter, et al.; "Structure-Based Design and Synthesis of a Thyroid Hormone Receiptor (TR) Antagonist," Endocrinology (2002), vol. 143, No. 2, pp. 517-524.

Koehler, et al.; "Thyroid Receptor Ligands. 6. A High Affinity "Direct Antagonist" Selective for the Thyroid Hormone Receptor," J. Med. Chem. (2006), vol. 49, pp. 6635-6637.

Schapira, et al.; "Discovery of Diverse Thyroid Hormone Receptor Antagonists by High-Throughput Docking," PNAS (2003), vol. 100, No. 12, pp. 7354-7359.

Webb, et al.; "Design of Thyroid Hormone Receptor Antagonists From First Principles," Journal of Steroid Biochemistry & Molecular Biology (2003), vol. 83, pp. 59-73.

International Search Report, dated Apr. 23, 2015, in PCT/US15/14555, filed Feb. 5, 2015.

Written Opinion of the International Searching Authority, dated Apr. 23, 2015, in PCT/US15/14555, filed Feb. 5, 2015.

(Continued)

*Primary Examiner* — Sahar Javanmard
(74) *Attorney, Agent, or Firm* — Dunlap Codding, P.C.

(57) ABSTRACT

Compositions for use in methods of treating and/or inhibiting a pathologic ocular condition, as well as methods of producing and using same, are disclosed.

5 Claims, 29 Drawing Sheets
(13 of 29 Drawing Sheet(s) Filed in Color)
Specification includes a Sequence Listing.

(56) References Cited

OTHER PUBLICATIONS

Grover, et al.; "Pharmacological Profile of the Thyroid Hormone Receptor Antagonist NH3 in Rats," Journal of Pharmacology and Experimental Therapeutics; (2007), vol. 332, No. 1, pp. 385-390.
Johnson, et al.; "A Quantitative High Throughput Screen Identifies Novel Inhibitors of the Interaction of Thyroid Receptor Beta With a Peptide of Steroid Receptor Coactivator 2," Journal of Biomelcular Screening (2011), vol. 16, No. 6; pp. 618-627 (Abstract).
Bergh, et al.; "Integrin $\alpha v \beta 3$ Contains a Cell Surface Receptor Site for Thyroid Hormone that Is Linked to Activation of Mitogen-Activated Protein Kinase and Induction of Angiogenesis," Endocrinology (2005) vol. 146, No. 7, pp. 2864-2871.
Brent, Gregory A.; "Mechanisms of Thyroid Hormone Action," The Journal of Clinical Investigation, (2012), vol. 122, No. 9, pp. 3035-3043.
Lazar, et al.; "Nuclear Thyroid Hormone Receptors," J. Clin. Invest. (1990), vol. 86, pp. 1777-1782.

\* cited by examiner

HY-4

A

B

A  MLS000389544-01

B  MLS000517530-01

C

D  MLS001003365-01

A    1-3992

B    2-274

C    2-284

D    2-1060

F

G

H

I

A

B

C

D

NH-3

1-850

```
SEQUENCE LISTING

<160> NUMBER OF SEQ ID NOS: 6

<210> SEQ ID NO 1
<211> LENGTH: 21
<212> TYPE: DNA
<213> ORGANISM: Mus musculus

<400> SEQUENCE: 1
tgaaagagtg ggaaaggatg g                                              21

<210> SEQ ID NO 2
<211> LENGTH: 22
<212> TYPE: DNA
<213> ORGANISM: Mus musculus

<400> SEQUENCE: 2
caccaagaca gaaagagtag gg                                             22

<210> SEQ ID NO 3
<211> LENGTH: 20
<212> TYPE: DNA
<213> ORGANISM: Mus musculus

<400> SEQUENCE: 3
gctacttcgt tctgggacac                                                20

<210> SEQ ID NO 4
<211> LENGTH: 22
<212> TYPE: DNA
<213> ORGANISM: Mus musculus

<400> SEQUENCE: 4
caaatctcac attgccaaag gg                                             22

<210> SEQ ID NO 5
<211> LENGTH: 20
<212> TYPE: DNA
<213> ORGANISM: Mus musculus

<400> SEQUENCE: 5
```

```
gcaaactttg ctttccctgg                                              20

<210> SEQ ID NO 6
<211> LENGTH: 20
<212> TYPE: DNA
<213> ORGANISM: Mus musculus

<400> SEQUENCE: 6
caagggcata tccaacaaca                                              20
```

COMPOSITIONS FOR TREATING RETINAL DEGENERATION AND METHODS OF PRODUCTION AND USE THEREOF

CROSS REFERENCE TO RELATED APPLICATIONS/INCORPORATION BY REFERENCE STATEMENT

This application is a US national stage application filed under 35 USC § 371 of International Application No. PCT/US2015/014555, filed Feb. 5, 2015; which claims priority to US provisional application U.S. Ser. No. 61/935,919, filed Feb. 5, 2014. The entire contents of the above-referenced patent applications are hereby expressly incorporated herein by reference.

STATEMENT REGARDING FEDERALLY SPONSORED RESEARCH OR DEVELOPMENT

This invention was made with government support under Contract Number R01EY019490 awarded by the National institutes of Health (NIH). The government has certain rights in the invention.

BACKGROUND

Rod and cone photoreceptors degenerate under a variety of pathological conditions, including a wide array of hereditary retinal diseases, such as but not limited to, retinitis pigmentosa, macular degeneration, and cone-rod dystrophies. Defects in a large number of genes are linked to inherited retinal degenerative disorders, including but not limited to, those encoding enzymes involved in the recycling of 11-cis retinal in the retinal pigment epithelium (RPE), retinoid isomerase (RPE65) and lecithin retinol acyltransferase (LRAT), and the phototransduction-associated proteins (opsins, subunits of transducin, cGMP phosphodiesterase PDE6, guanylate cyclase, and the cyclic nucleotide-gated channel). There are currently no effective treatments for human retinal dystrophies. Despite a high genetic heterogeneity, the degenerating photoreceptors show common cellular disorder features, including but not limited to, oxidative damage, endoplasmic reticulum stress, and apoptosis.

Thyroid hormone (TH) signaling regulates cell proliferation, differentiation, and apoptosis. The role of TH signaling in the retina regarding its regulation of cone opsin expression and patterning has been well documented. Most mammals possess dichromatic color vision that is mediated by two opsins with peak sensitivities to medium-long (M, green) and short (S, blue) wavelengths of light. In the mouse, M- and S-opsins are expressed in opposing gradients such that varying amounts of both opsins are co-expressed in cones in mid-retinal regions, whereas M-opsin predominates in dorsal (superior) regions, and S-opsin predominates in ventral (inferior) regions (FIG. 1). During development and in the adult postmitotic retina, TH signaling via its receptor type β2 (TRβ2) suppresses expression of S-opsin, induces expression of M-opsin, and promotes the dorsal-ventral opsin patterning. Importantly, TH signaling has been associated with cone viability. Triiodothyronine (T3) treatment was shown to cause cone death in mice and this effect was reversed by deletion of TRβ2 gene. Excessive TH signaling was also shown to induce auditory defects and cochlear degeneration in mice. TH signaling has been associated with apoptosis of a variety of human cell lines, including but not limited to lymphocytes, breast cancer cells, HeLa cells, and pituitary tumor cells; TH signaling has also been well documented in apoptotic tissue remodeling during anuran metamorphosis.

As stated herein above, while it is known that photoreceptors degenerate in a wide array of hereditary retinal diseases, there is currently no treatment available for these retinal degenerations. Thus, there is a great need in the art for new compositions and methods for treating and/or inhibiting pathologic ocular conditions.

BRIEF DESCRIPTION OF THE DRAWINGS

The patent or application file contains at last one drawing executed in color. Copies of this patent or patent application publication with color drawing(s) will be provided by the Office upon request and payment of the necessary fee.

As shown in FIG. 25, left panel, treatment with T3 increased M-opsin expression in Weri cells, and this effect was inhibited by NH-3 in a dose-dependent pattern (right panel).

DETAILED DESCRIPTION

Figure 1:
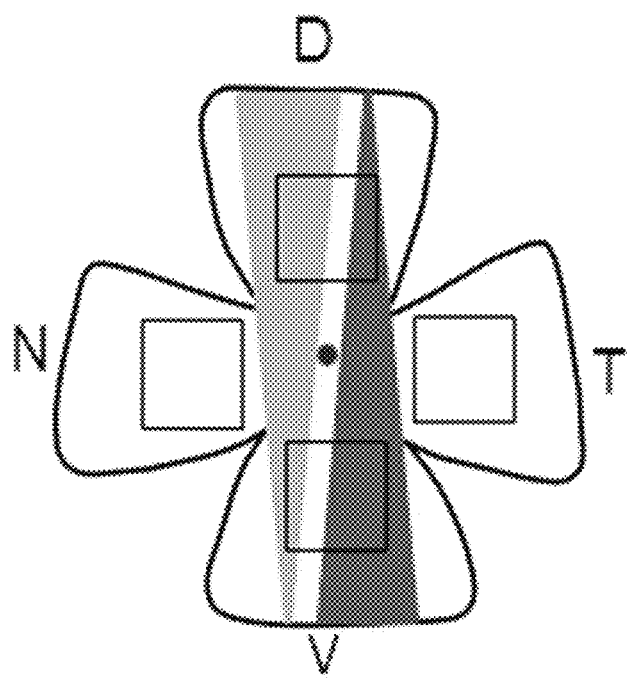
FIG. 1 contains a diagram of a mouse retinal whole mount showing dorsal (D), nasal (N), ventral (V), and temporal (T) areas. The colored parts illustrate the dorsal-ventral gradients of M-opsin (green) and S-opsin (blue) co-expression in the wild-type mouse cones, with M-opsin declining dorsal to ventral and S-opsin declining ventral to dorsal. The square in the center of each quadrant represents the area where images were taken for cone density quantification.

The presently disclosed inventive concepts include methods for treating and/or inhibiting cone photoreceptor degeneration in pathologic ocular conditions involving retinal degeneration such as, but not limited to, age-related macular degeneration (AMD), Stargardt disease, and retinitis pigmentosa and related diseases such as Usher syndrome, Leber's congenital amaurosis, achromatopsia, rod-cone and cone-rod dystrophies, Bardet-Biedel syndrome, juvenile retinoschisis, choroideremia, diabetic retinopathy, and others.

Before describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

All patents, published patent applications, and non-patent publications mentioned in the present specification are indicative of the level of skill of those skilled in the art to which the presently disclosed inventive concepts pertain. All patents, published patent applications, and non-patent publications referenced in any portion of this application are herein expressly incorporated by reference in their entireties to the same extent as if each individual patent or publication was specifically and individually indicated to be incorporated by reference.

All of the compounds, compositions and methods of production and application thereof disclosed herein can be made and executed without undue experimentation in light of the present disclosure. While the compositions and methods of the presently disclosed inventive concepts have been described in terms of particular embodiments, variations may be applied to the compounds, compositions and/or methods and in the steps or in the sequence of steps of the method described herein without departing from the concept, spirit and scope of the inventive concepts disclosed herein. All such similar substitutes and modifications apparent to those of skilled in the art are deemed to be within the spirit, scope, and concept of the inventive concepts as disclosed herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. For example but not by way of limitation, when the term "about" is utilized, the designated value may vary by plus or minus twelve percent, or by plus or minus eleven percent, or by plus or minus ten percent, or by plus or minus nine percent, or by plus or minus eight percent, or by plus or minus seven percent, or by plus or minus six percent, or by plus or minus five percent, or by plus or minus four percent, or by plus or minus three percent, or by plus or minus two percent, or by plus or minus one percent, or by plus or minus one-half percent.

As used herein, the term "substantially" means that the subsequently described event or circumstance completely occurs or that the subsequently described event or circumstance occurs to a great extent or degree. In some embodiments for example, the term "substantially" means that the subsequently described event or circumstance occurs at least 75% of the time, or at least 80% of the time, or at least 85% of the time, or at least 90% of the time, or at least 95% of the time, or at least 98% of the time.

The term "pharmaceutically acceptable" refers to compounds and compositions which are suitable for administration to humans and/or mammals without undue adverse side effects such as toxicity, irritation and/or allergic response commensurate with a reasonable benefit/risk ratio.

A "therapeutically effective amount" of one or more therapeutic compounds of the presently disclosed inventive concepts refers to an amount which is effective in preventing, controlling, reducing, and/or inhibiting loss of cone photoreceptors. The term "controlling" is intended to refer to all processes wherein there may be a slowing, interrupting, arresting, and/or stopping of the progression of the cone photoreceptor loss and does not necessarily indicate a total elimination of the cone photoreceptor loss. The term "therapeutically effective amount" is further meant to define an amount resulting in the improvement of any parameters or clinical symptoms characteristic of cone photoreceptor loss or retinal degeneration. The actual dose will vary with the patient's overall condition, the seriousness of the symptoms, and counter indications. As used herein, the term "therapeutically effective amount" also means the total amount of each active component of the pharmaceutical composition or method that is sufficient to show a meaningful patient benefit, e.g., a reduction of cone photoreceptor loss or an improvement in vision or reduction in vision degeneration.

A "therapeutically effective amount" is generally an amount of a therapeutic compound which is sufficient to exhibit a detectable therapeutic effect without excessive adverse side effects (such as toxicity, irritation and allergic response) commensurate with a reasonable benefit/risk ratio when used in the manner of the inventive concepts disclosed herein. The therapeutic effect may include, for example but not by way of limitation, a partial or complete elimination of retinal cone degeneration. The therapeutically effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the therapeutically effective amount for a given situation can be determined by one of ordinary skill in the art using routine experimentation based on the information provided herein.

By "biologically active" is meant the ability to modify the physiological system of an organism without reference to how the active agent has its physiological effects.

The terms "subject" and "patient" are used interchangeably herein and will be understood to refer to a warm blooded animal, particularly a mammal, which has retinal cone photoreceptors. Non-limiting examples of animals within the scope and meaning of this term include animals that have cone photoreceptors, including, but not limited to, humans, guinea pigs, dogs, cats, rats, mice, horses, goats, llamas, cattle, sheep, zoo animals, New World monkeys, Old World monkeys, and apes.

The term "treatment" refers to therapeutic treatments. The term "treating" or "reducing" generally refers to administering the composition to a patient having some degree of retinal degeneration for therapeutic purposes. "Prevention," "preventing," "inhibition," or "inhibiting" generally refers to prophylactic or preventative treatment measures, for example but not by way of limitation, subjects who may not yet have the disease or condition but may be predisposed to contracting the disease or developing the condition.

The terms "therapeutic composition" and "pharmaceutical composition" refer to a therapeutic compound-containing composition that may be administered to a subject by any method known in the art or otherwise contemplated herein, wherein administration of the composition brings about a therapeutic effect as described elsewhere herein. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the presently disclosed inventive concepts may be designed to provide delayed, controlled, extended, and/or sustained release using formulation techniques which are well known in the art.

The term "topical" is used herein to define a mode of administration through an epithelial surface, such as but not limited to, a material that is administered by being applied externally to the eye. A non-limiting example of topical administration is through the use of eyedrops.

As used herein, the term "concurrent therapy" is used interchangeably with the terms "combination therapy" and "adjunct therapy," and will be understood to mean that the subject in need of treatment is treated or given another drug in conjunction with the pharmaceutical compositions of the presently disclosed inventive concepts. This concurrent therapy can be sequential therapy, where the patient is treated first with one composition and then the other composition. Alternatively, the two compositions can be given simultaneously. Non-limiting examples of combination therapies in accordance with the presently disclosed inventive concepts include a combination of two or more of the therapeutic compounds described or otherwise contemplated herein, one or more of said therapeutic compounds in combination with one or more other ocular treatments, or one or more of said therapeutic compounds in combination with another drug given to treat a particular condition.

Turning now to the presently disclosed inventive concepts, certain non-limiting embodiments thereof are directed to compounds that can be utilized for inhibiting and/or suppressing thyroid hormone signaling in the retina, thereby preserving the viability of cone photoreceptors therein; this protection of photoreceptor viability results in reduced retinal degeneration and preservation of retinal function. The compounds may function (for example, but not by way of limitation) by inhibiting binding of TH to its receptor (such as, but not limited to, TRβ2), or by any other TH antagonistic effect. The compounds may be utilized to treat and/or inhibit cone photoreceptor degeneration in any pathologic ocular condition involving retinal degeneration; non-limiting examples of such conditions include age-related macular degeneration (AMD), Stargardt disease, and retinitis pigmentosa, as well as related diseases such as Usher syndrome, Leber's congenital amaurosis, achromatopsia, a rod-cone dystrophy, a cone-rod dystrophy, Bardet-Biedel syndrome, juvenile retinoschisis, choroideremia, diabetic retinopathy, and the like.

The compounds of the presently disclosed inventive concepts include thyroid hormone receptor antagonists, such as but not limited to, antagonists of thyroid hormone receptor (such as, but not limited to, TRβ2). Specific classes of compounds that fall within the scope of the presently disclosed inventive concepts are described in detail herein below in the Examples; particular non-limiting examples of TH antagonistic compounds that can be used to inhibit action of TH in accordance with the presently disclosed inventive concepts are shown in Formulas (I)-(II) and FIGS. 15-24 and are further described in Example 2. For example, but not by way of limitation, the antagonist of thyroid hormone receptor (such as, but not limited to, TRβ2) may be represented by Formula (I):

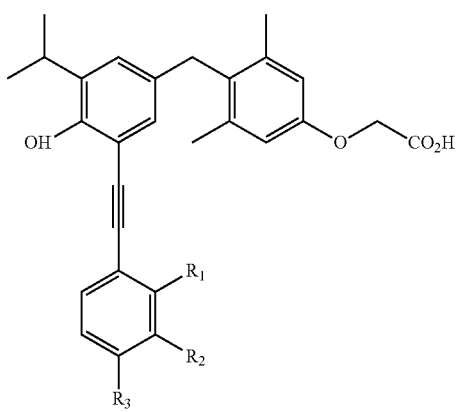

Formula (I)

wherein: (i) $R_1$ is $CF_3$, and $R_2$ and $R_3$ are H; (ii) $R_2$ is $CF_3$ or $NO_2$, and $R_1$ and $R_3$ are H; or (iii) $R_3$ is $CF_3$, $NO_2$, $N_3$, $COCH_3$, F, or $CH_2N_3$, and $R_1$ and $R_3$ are H.

In an alternative example, the antagonist of thyroid hormone receptor (such as, but not limited to, TRβ2) of the ophthalmic composition may be represented by Formula (II):

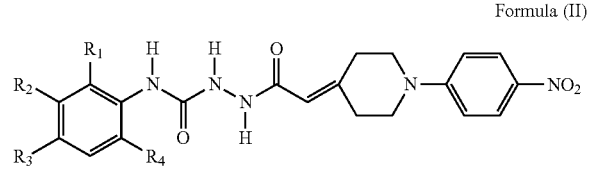

Formula (II)

wherein: (i) $R_1$ is $CH(CH_3)_2$ or $CH_2CH_3$, and $R_2$, $R_3$, and $R_4$ are H; (ii) $R_2$ is $CF_3$, and $R_1$, $R_3$, and $R_4$ are H; (iii) $R_3$ is $CF_3$ or $OCH_3$, and $R_1$, $R_2$, and $R_3$ are H; (iv) $R_1$ is $CH(CH_3)_2$, $R_4$ is $CH_3$, and $R_2$ and $R_3$ are H; (v) $R_2$ is $CH_3$, $R_4$ is $OCH_3$, and $R_1$ and $R_3$ are H; (vi) $R_2$ and $R_3$ are F, and $R_1$ and $R_4$ are H; or (vii) $R_1$, $R_3$, and $R_4$ are $CH_3$, and $R_2$ is H.

Figure 24:
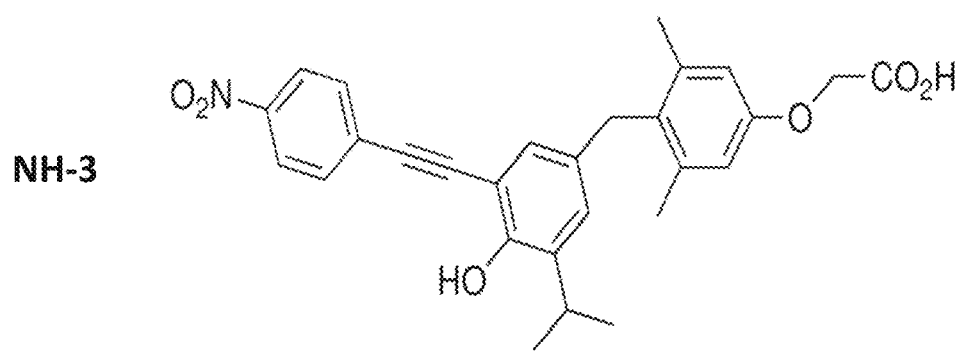
FIG. 24 contains panels A-B that illustrate the structures of compounds referred to herein as "NH-3" and "1-850," respectively, which are utilized as TH receptor antagonists in accordance with alternative embodiments of the presently disclosed inventive concepts.
Figure 24:
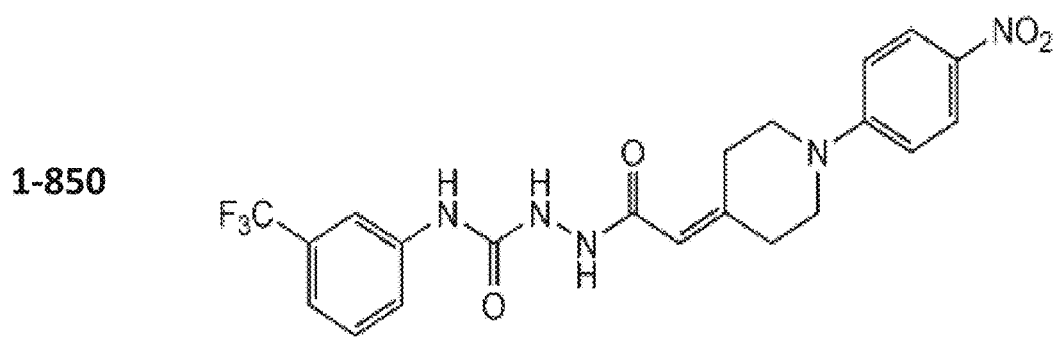

In other non-limiting examples, the active compound may be the thyroid hormone receptor antagonist {4-[4-Hydroxy-3-isopropyl-5-(4-nitrophenylethynyl)benzyl]-3,5-dimethyl phenoxy} acetic Acid (referred to herein as "NH-3" and shown in the upper structure of FIG. 24) and/or the thyroid hormone receptor antagonist 2-(2-(-(4-Nitrophenyl)-4-piperidinylidene)acetyl-N-(3-(trifluoromethyl)phenyl)-1-hydrazine Carboxamide (referred to herein as "1-850" and shown in the lower structure of FIG. 24).

However, it is not intended that the presently disclosed inventive concepts be limited to the compounds shown in FIGS. 15-24, Formulas (I)-(II), or Example 2 or to those described elsewhere herein. Any compound known or otherwise contemplated in the art that functions to inhibit and/or suppress thyroid hormone signaling in the retina may be utilized; thus, the compounds of FIGS. 15-24, Formulas (I)-(II), and Example 2 are provided for purposes of illustration only and do not limit the scope of the presently disclosed inventive concepts in any manner.

Certain non-limiting embodiments of the presently disclosed inventive concepts are directed to pharmaceutical compositions that include one or more of the compounds that inhibit and/or suppress thyroid hormone signaling in the retina, in combination with at least one pharmaceutically acceptable carrier. Particular non-limiting examples of pharmaceutical (therapeutic) compositions formulated in accordance with the presently disclosed inventive concepts include: (a) a pharmaceutical composition comprising a therapeutic compound effective in inhibiting TH signaling (as described or otherwise contemplated herein) in combination with at least one pharmaceutically acceptable carrier; (b) a pharmaceutical composition comprising at least two therapeutic compounds effective in inhibiting TH signaling in combination with at least one pharmaceutically acceptable carrier; and (c) a pharmaceutical composition comprising at least one therapeutic compound effective in inhibiting TH signaling in combination with at least one other therapeutically active agent and at least one pharmaceutically acceptable carrier.

The compound(s) effective in inhibiting TH signaling may be present in the pharmaceutical compositions of the presently disclosed inventive concepts at any concentration that allows the pharmaceutical composition to function in accordance with the presently disclosed inventive concepts; for example, but not by way of limitation, the compound(s) may be present in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.10% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the presently disclosed inventive concepts.

Suitable carriers, vehicles, and other components that may be included in the formulation are described, for example, in *Remington: The Science and Practice of Pharmacy*, 21$^{st}$ Ed. The term "pharmaceutically acceptable" means that the carrier is a non-toxic material that does not interfere with the effectiveness of the biological activity of the active ingredient(s). The characteristics of the carrier will depend on various factors, including but not limited to, the route of administration.

For example, but not by way of limitation, the therapeutic compounds may be dissolved in a physiologically acceptable pharmaceutical carrier and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof.

For reconstitution of a lyophilized product in accordance with the presently disclosed inventive concepts, a sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the therapeutic compound(s) and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the presently disclosed inventive concepts may include the incorporation or entrapment of the therapeutic compound(s) in various types of drug delivery systems that function to provide targeted delivery, controlled release, and/or increased half-life to the therapeutic compound(s). For example, but not by way of limitation, it is possible to entrap the therapeutic compound(s) in microcapsules prepared by coacervation techniques or by interfacial polymerization (for example, hydroxymethylcellulose or gelatin-microcapsules and poly-(methylmethacylate) microcapsules, respectively). It is also possible to entrap the therapeutic compound(s) in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the therapeutic compound(s) is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. No. 4,235,871, U.S. Pat. No. 4,501,728; U.S. Pat. No. 4,837,028; and U.S. Pat. No. 4,737,323, the entire contents of each of which are incorporated herein by reference.

In another particular, non-limiting example, the pharmaceutical compositions of the presently disclosed inventive concepts may be incorporated into particles of one or more polymeric materials, as this type of incorporation can be useful in controlling the duration of action of the therapeutic compounds by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(l-aspartamide), and combinations thereof.

In certain non-limiting embodiments, the pharmaceutical composition may be in the form of an ophthalmic composition for topical application to an eye of a subject. The term "ophthalmic composition" as used herein will be understood to refer to any composition formulated for direct and local administration to an eye of a patient. Said composition may be formulated for topical administration to the eye or for injection into the eye (i.e., intravitreal or intraocular injection). The ophthalmic composition may be provided in any formulation that allows for local administration thereof to the eye and allows the therapeutic compounds to function in accordance with the presently disclosed inventive concepts. For example, but not by way of limitation, the ophthalmic composition may be provided in the form of a solution, drops, a mist/spray, plasters and pressure sensitive adhesives, an ointment, a lotion, a cream, a gel, lyophilized/spray-dried forms, and the like. In one particular non-limiting embodiment, the ophthalmic composition is provided in a form for topical application, such as but not limited to, an eyedrop formulation. The ophthalmic compositions of the presently disclosed inventive concepts typically vary according to the particular active agent(s) used, the preferred drug release profile, the condition being treated, and/or the medical history of the patient. In addition, the ophthalmic compositions of the presently disclosed inventive concepts may be designed to provide delayed, controlled, extended, and/or sustained release using formulation techniques which are well known in the art.

The pharmaceutical compositions described or otherwise contemplated herein may further comprise at least one delivery agent that assists in delivery of the inhibitor to a desired site of delivery; for example but not by way of limitation, at least one delivery agent may be included in an ophthalmic composition to assist in the penetration of a surface of an eye; in certain embodiments, the delivery agent may assist in delivery to a retina of the eye. For example, in order for a topical application to be effective, the composition may need to be able to penetrate the surface of the eye so that it can travel to the desired tissue. This may include penetrating the conjunctiva and/or the cornea. Also, the penetration rate must be sufficient to impart an effective dose. Many drugs do not possess a requisite penetration ability with regard to the tissues of the eye. It should be noted that the external layers of the eye are quite different from the tissues encountered in the stomach and intestinal tract. Thus, while a certain drug may be readily absorbed in the intestines and introduced into the blood supply for systemic administration, the same drug may be incapable of being absorbed by or passing through the substantially avascular outer layers of the conjunctiva or cornea at a minimally acceptable therapeutic concentration. The mechanism of transport or uptake of the drug is entirely different for topical administration than for oral administration.

When the ophthalmic composition is formulated for administration by injection, the composition may be in the form of a pyrogen-free, aqueous solution or suspension. The preparation of such solutions, having due regard to pH, isotonicity, stability, and the like, is well within the skill of one of ordinary skill in the art. Suitable carriers include, but are not limited to, biocompatible and pharmaceutically acceptable phosphate buffered saline solutions, which are particularly isotonic. For example, but not by way of limitation, a particular ophthalmic composition may contain, in addition to the therapeutic compound(s), an isotonic vehicle such as Sodium Chloride Injection, Ringer's Injection, Dextrose Injection, Dextrose and Sodium Chloride Injection, Lactated Ringer's Injection, or other vehicles as known in the art. In general, the material for intravenous injection in humans should conform to regulations established by the US Food and Drug Administration, which are available to those in the field.

In addition to the ophthalmic administrations discussed in detail herein above, the therapeutic compositions of the presently disclosed inventive concepts may be formulated for administration by any other method known or otherwise contemplated in the art, as long as the route of administration allows for delivery of the therapeutic compounds so that the compounds can function in accordance with the presently disclosed inventive concepts. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the presently disclosed inventive concepts is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically acceptable carrier, diluent, or other agent for mixing with the therapeutic compound(s) for preparation of the pharmaceutical composition. The kit may also include instructions packaged with the reagents for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition(s). When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of active material calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the therapeutic compound(s) may sometimes be a minor component (from about 0.1 to about 50% by weight, such as but not limited to, from about 1 to about 40% by weight) with the remainder being various vehicles or carriers and processing aids helpful for forming the desired dosing form.

As is evident from the above, the therapeutic compounds of the presently disclosed inventive concepts find uses as inhibitors of cone photoreceptor degeneration for the treatment, inhibition, mitigation, and/or prevention of degenerative retinal disorders. Thus, certain non-limiting embodiments of the presently disclosed inventive concepts include methods of treating, inhibiting, and/or reducing the occurrence of retinal degeneration due to cone photoreceptor loss. One particular non-limiting embodiment includes a method of treating, inhibiting, and/or reducing the occurrence of one or more pathologic ocular conditions associated with cone photoreceptor degeneration (e.g., a retinal degenerative condition) in a subject in need thereof. In the method, one or more of any of the pharmaceutical compositions described or otherwise contemplated herein is administered to a subject (such as, but not limited to, a mammal) that is experiencing retinal degeneration or that is predisposed to developing retinal degeneration. The pharmaceutical composition(s) is administered to the subject in an amount effective to inhibit, control, and/or reduce thyroid hormone signaling in the retina of at least one eye of the subject.

The pathologic ocular condition may be any of the conditions described herein above, and the pathologic ocular condition may be characterized by retinal degeneration and/or photoreceptor death. In one embodiment, the pharmaceutical composition may be administered topically to an eye of the subject (such as, but not limited to, as an eyedrop). In an alternative embodiment, the pharmaceutical composition may be administered by ocular injection.

The amount of the therapeutic composition that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific retinal and/or ocular disease or other condition involved; the degree, involvement, and/or severity of the retinal degeneration; the response of the individual subject; the particular therapeutic compound(s) administered; the mode of administration; the bioavailability characteristics of the preparation administered; the dose regimen selected; the use of concomitant medication; and other relevant circumstances. A therapeutically effective amount of a pharmaceutical composition of the presently disclosed inventive concepts also refers to an amount of the therapeutic compound which is effective in controlling and/or reducing the cone photoreceptor loss.

For example, but not by way of limitation, the therapeutically effective amount of a therapeutic compound used in the presently disclosed inventive concepts will generally contain sufficient active ingredient to deliver in a range of from about 0.01 µg/kg to about 10 mg/kg (weight of active ingredient/body weight of patient). For example, but not by way of limitation, the composition will deliver about 0.1 µg/kg to about 5 mg/kg, and more particularly about 1 µg/kg to about 1 mg/kg.

Practice of the method of the presently disclosed inventive concepts may include administering to a subject a therapeutically effective amount of the pharmaceutical composition (containing the TH signaling inhibiting compound) in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the presently disclosed inventive concepts.

The presently disclosed inventive concepts include, in at least certain, non-limiting embodiments, an ophthalmic composition formulated for direct and local administration to an eye of a subject. The ophthalmic composition comprises at least one therapeutic compound that is an antagonist of thyroid hormone receptor (such as, but not limited to, TRβ2) and a pharmaceutically acceptable carrier.

The at least one antagonist of thyroid hormone receptor (such as, but not limited to, TRβ2) of the ophthalmic composition may be represented by Formula (I):

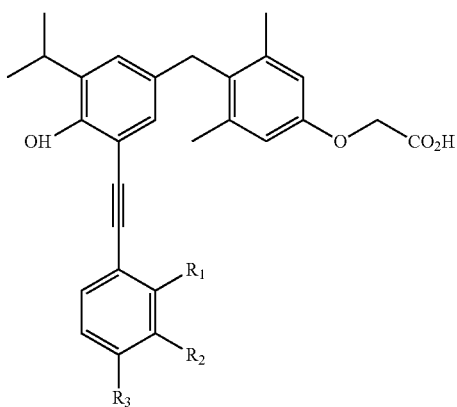

Formula (I)

wherein: (i) $R_1$ is $CF_3$, and $R_2$ and $R_3$ are H; (ii) $R_2$ is $CF_3$ or $NO_2$, and $R_1$ and $R_3$ are H; or (iii) $R_3$ is $CF_3$, $NO_2$, $N_3$, $COCH_3$, F, or $CH_2N_3$, and $R_1$ and $R_3$ are H.

Alternatively, the at least one antagonist of thyroid hormone receptor (such as, but not limited to, TRβ2) of the ophthalmic composition may be represented by Formula (II):

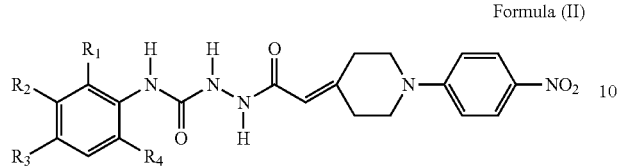

Formula (II)

wherein: (i) R$_1$ is CH(CH$_3$)$_2$ or CH$_2$CH$_3$, and R$_2$, R$_3$, and R$_4$ are H; (ii) R$_2$ is CF$_3$, and R$_1$, R$_3$, and R$_4$ are H; (iii) R$_3$ is CF$_3$ or OCH$_3$, and R$_1$, R$_2$, and R$_3$ are H; (iv) R$_1$ is CH(CH$_3$)$_2$, R$_4$ is CH$_3$, and R$_2$ and R$_3$ are H; (v) R$_2$ is CH$_3$, R$_4$ is OCH$_3$, and R$_1$ and R$_3$ are H; (vi) R$_2$ and R$_3$ are F, and R$_1$ and R$_4$ are H; or (vii) R$_1$, R$_3$, and R$_4$ are CH$_3$, and R$_2$ is H.

The therapeutic compound of the ophthalmic composition may comprise {4-[4-Hydroxy-3-isopropyl-5-(4-nitrophenylethynyl)benzyl]-3,5-dimethylphenoxy} acetic Acid and/or 2-(2-(-(4-Nitrophenyl)-4-piperidinylidene)acetyl-N-(3-(trifluoromethyl)phenyl)-1-hydrazine Carboxamide. The ophthalmic composition of any one of the above may be further defined as being formulated for topical administration to or ocular injection into the eye of the subject. The ophthalmic composition of any one of the above may be further defined as an eyedrop. The ophthalmic composition of any one of the above may further comprise at least one delivery agent that assists in delivery of the therapeutic compound to a desired site of delivery.

The presently disclosed inventive concepts include, in at least certain non-limiting embodiments, a kit comprising at least one of the above ophthalmic compositions. The at least one ophthalmic composition may be present in the kit in any form, including but not limited to, in at least one unit dosage form.

The presently disclosed inventive concepts include, in at least certain non-limiting embodiments, a pharmaceutical composition for use in a method of treating, inhibiting, and/or reducing the occurrence of a pathologic ocular condition associated with cone photoreceptor degeneration in a subject in need thereof. The pharmaceutical composition comprises at least one antagonist of thyroid hormone receptor (such as, but not limited to, TRβ2); the method comprises the step of administering to the subject the pharmaceutical composition, wherein the subject is suffering from or is predisposed to the pathologic ocular condition, and wherein the pharmaceutical composition is administered in an amount effective to inhibit and/or reduce thyroid hormone signaling in the retina of at least one eye of the subject.

The pathologic ocular condition may be characterized by at least one of retinal degeneration and photoreceptor death. The pathologic ocular condition may be at least one of age-related macular degeneration, Stargardt disease, retinitis pigmentosa, Usher syndrome, Leber's congenital amaurosis, achromatopsia, a rod-cone dystrophy, a cone-rod dystrophy, Bardet-Biedel syndrome, juvenile retinoschisis, choroideremia, and diabetic retinopathy. The pharmaceutical composition of any of the above embodiments may be formulated for topical administration to or ocular injection into at least one eye of the subject. The at least one antagonist of thyroid hormone receptor (such as, but not limited to, TRβ2) of any of the above pharmaceutical compositions may be represented by Formula (I):

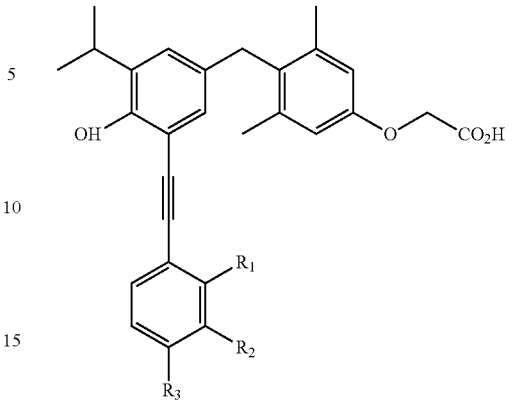

Formula (I)

wherein: (i) R$_1$ is CF$_3$, and R$_2$ and R$_3$ are H; (ii) R$_2$ is CF$_3$ or NO$_2$, and R$_1$ and R$_3$ are H; or (iii) R$_3$ is CF$_3$, NO$_2$, N$_3$, COCH$_3$, F, or CH$_2$N$_3$, and R$_1$ and R$_3$ are H.

Alternatively, the at least one antagonist of thyroid hormone receptor (such as, but not limited to, TRβ2) of any of the above pharmaceutical compositions may be represented by Formula (II):

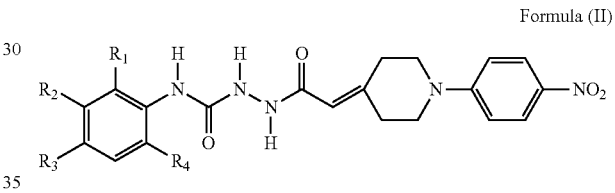

Formula (II)

wherein: (i) R$_1$ is CH(CH$_3$)$_2$ or CH$_2$CH$_3$, and R$_2$, R$_3$, and R$_4$ are H; (ii) R$_2$ is CF$_3$, and R$_1$, R$_3$, and R$_4$ are H; (iii) R$_3$ is CF$_3$ or OCH$_3$, and R$_1$, R$_2$, and R$_3$ are H; (iv) R$_1$ is CH(CH$_3$)$_2$, R$_4$ is CH$_3$, and R$_2$ and R$_3$ are H; (v) R$_2$ is CH$_3$, R$_4$ is OCH$_3$, and R$_1$ and R$_3$ are H; (vi) R$_2$ and R$_3$ are F, and R$_1$ and R$_4$ are H; or (vii) R$_1$, R$_3$, and R$_4$ are CH$_3$, and R$_2$ is H.

The at least one antagonist of thyroid hormone receptor (such as, but not limited to, TRβ2) of any of the above pharmaceutical compositions may be {4-[4-Hydroxy-3-isopropyl-5-(4-nitrophenylethynyl)benzyl]-3,5-dimethylphenoxy} acetic Acid and or 2-(2-(-(4-Nitrophenyl)-4-piperidinylidene)acetyl-N-(3-(trifluoromethyl)phenyl)-1-hydrazine Carboxamide. The pharmaceutical composition of any of the above may comprise at least one delivery agent that assists in delivery of the therapeutic compound to the at least one eye of the subject.

The presently disclosed inventive concepts include, in at least certain non-limiting embodiments, a method of treating, inhibiting, and/or reducing the occurrence of a pathologic ocular condition associated with cone photoreceptor degeneration in a subject in need thereof. The method comprises the step of administering to the subject a pharmaceutical composition comprising at least one antagonist of thyroid hormone receptor (such as, but not limited to, TRβ2), wherein the subject is suffering from or is predisposed to the pathologic ocular condition, and wherein the pharmaceutical composition is administered in an amount effective to inhibit and/or reduce thyroid hormone signaling in the retina of at least one eye of the subject. The pharmaceutical composition used in the method may be any of the pharmaceutical compositions described hereinabove or otherwise contemplated herein. The pathologic ocular condition may be characterized by at least one of retinal degeneration and photoreceptor death, and/or may be at least one of age-related macular degeneration, Stargardt disease, retinitis pigmentosa, Usher syndrome, Leber's congenital amaurosis, achromatopsia, a rod-cone dystrophy, a cone-rod dystrophy, Bardet-Biedel syndrome, juvenile retinoschisis, choroideremia, and diabetic retinopathy. The method may include administration of the pharmaceutical composition topically or by injection to at least one eye of the subject. The subject may be a mammal. The pharmaceutical composition may further comprises at least one delivery agent that assists in delivery of the therapeutic compound to the at least one eye of the subject.

EXAMPLES

The presently disclosed inventive concepts, having now been generally described, will be more readily understood by reference to the following examples and embodiments, which are included merely for purposes of illustration of certain aspects and embodiments of the presently disclosed inventive concepts, and are not intended to be limiting. The following description includes various therapeutic compounds of the presently disclosed inventive concepts, as well as methods of producing and using same, and are to be construed, as noted above, only as illustrative, and not limitations of the disclosure in any way whatsoever. Those skilled in the art will promptly recognize appropriate variations from the compounds and procedures.

Example 1

Cone phototransduction and survival of cones in the retinas of mammals is essential for daylight vision, color vision, and visual acuity. Progressive cone degeneration in pathologic ocular conditions involving retinal degeneration such as (but not limited to) age-related macular degeneration (AMD), retinitis pigmentosa, Stargardt disease, and recessive cone dystrophies is a major cause of blindness. AMD is the leading cause of blindness in elderly persons. There are currently no effective treatments available on the market for retinal degeneration. Certain embodiments of the presently disclosed inventive concepts are directed to methods that provide such treatment.

Thyroid hormone (TH) signaling, which regulates cell proliferation, differentiation, and apoptosis, plays a central role in cone opsin expression and patterning in the retina. The present example investigated how TH signaling affects cone viability in inherited retinal degeneration mouse models. To determine whether TH signaling affects cone viability in inherited retinal degeneration, cone death/survival in retinal degeneration mouse models was investigated following TH signaling suppression and stimulation. Rpe65$^{-/-}$ (a model of Leber's congenital amaurosis or LCA) and cpfl1 mice (PDE6C mutation, a model of achromatopsia), displaying fast and severe cone degeneration, were used to determine whether suppressing TH signaling with anti-thyroid treatment reduces cone degeneration. Cngb3$^{-/-}$ (a model of achromatopsia) and Gucy2e$^{-/-}$ (another model of LCA) mice, displaying relatively slow progressive and moderate cone degeneration, were used to determine whether stimulating TH signaling (with T3 treatment) deteriorates cones. It is shown herein that cone survival was greatly improved in Rpe65$^{-/-}$ and cpfl1 mice following TH signaling suppression, whereas cone degeneration was significantly increased in Cngb3$^{-/-}$ and Gucy2e$^{-/-}$ mice following TH signaling stimulation, demonstrating a protective role of suppressing TH signaling in cones.

It was found that cone density in Rpe65$^{-/-}$ and cpfl1 mice increased about 6-fold following anti-thyroid treatment. Cone density in Cngb3$^{-/-}$ and Gucy2e$^{-/-}$ mice decreased about 40% following T3 treatment. The effect of TH signaling on cone viability appears to be independent of its regulation on cone opsin expression. As shown below, this example demonstrates that suppressing TH signaling in retina dystrophy mouse models is protective of cones.

Materials and Methods of Example 1

Mice.

The Rpe65$^{-/-}$, Cngb3$^{-/-}$, and Gucy2e$^{-/-}$ mouse lines were generated using methods known in the art (Redmond et al., 1998; Ding et al. 2009; and Yang et al., 1999; respectively). The Cpfl1 mouse line was obtained from The Jackson Laboratory (Bar Harbor, Me.) and wild-type mice (C57BL/6) were purchased from Charles River Laboratories (Wilmington, Mass.). All mice were maintained under cyclic light (12-hour light-dark) conditions. Cage illumination was approximately 7 foot-candles during the light cycle. All animal maintenance and experiments were approved by the local Institutional Animal Care and Use Committee (University of Oklahoma Health Sciences Center, Oklahoma City, Okla.) and conformed to the guidelines on the care and use of animals adopted by the Society for Neuroscience and the Association for Research in Vision and Ophthalmology (Rockville, Md.).

Drug Treatments.

For anti-thyroid treatment, mother Rpe65$^{-/-}$ and cpfl1 mice were treated with methimazole (MMI) (Sigma-Aldrich, St. Louis, Mo., 0.05% wt/vol) and sodium perchlorate monohydrate (PM) (Sigma-Aldrich, 1.0% wt/vol) in drinking water, beginning on the day they delivered pups and the treatment (for both mother and pups) continued for 30 days. In a separate experiment, post-weaning cpfl1 mice received MMI and PM treatment for 30 days, beginning on P25. For T3 treatment, Cngb3$^{-/-}$ and Gucy2e$^{-/-}$ mice received T3 (Sigma-Aldrich, 0.1 µg/g body weight, subcutaneous injection once each day) or vehicle (saline) for 30 days, beginning on P1. At the end of the treatments, blood samples were collected for measurements of serum T3 levels, and eyes and retinas were collected for evaluating cone density and cone specific protein/mRNA expression. For T3-treated mice, blood samples were collected around 24 hours after the last injection.

Thyroid Hormone Measurement.

Serum triiodothyronine (T3) levels were analyzed using a mouse/rat T3 ELISA kit (Calbiotech Inc., Spring Valley, Calif.) with a total T3 detection limit at 0.25 ng/ml. Briefly, 25 µl of serum samples and standards with different T3 concentrations were added into the assigned wells, the assays were performed by following the manufacturer's instructions, and the absorbance of each well was read at 450 nm (SPECTRAMAX® 190 Microplate Spectrophotometer, Molecular Devices LLC, Sunnyvale, Calif.). The standard curve was generated by using a three-parameter exponential non-linear regression in SIGMAPLOT® software (Systat Software, Inc., San Jose, Calif.), and the sample T3 concentration was then calculated according to the three-parameter exponential equation.

Eye Preparation, Retinal Morphometric Analysis, Immunohistochemistry, and Confocal Microscopy.

Mouse retinal whole mounts or cross sections were prepared for immunohistochemical analysis as described previously (Ding et al., 2009; and Xu et al., 2011). For whole mount preparations, eyes were enucleated, marked at the superior pole with a green dye, and fixed in 4% paraformaldehyde (PFA) (Polysciences, Inc., Warrington, Pa.) in phosphate-buffered saline (PBS) (vol/vol) for 30 minutes at room temperature. The cornea and lens were then removed, and the eyes were fixed in 4% PFA in PBS (vol/vol) at room temperature for another 4-6 hours. The retina was then marked for orientation with a small cut left of the superior portion and isolated. For retinal cross sections, mouse eyes were enucleated (the superior portion of the cornea was marked for orientation before enucleation) and fixed in Prefer (Anatech Ltd., Battle Creek, Mich.) for 15 minutes at room temperature, and fixed eyes were then stored in 70% ethanol in water (vol/vol) until processed and embedded in paraffin. Paraffin sections (5 μm thickness) passing vertically through the retina (along the vertical meridian passing through the optic nerve head) were prepared using a Leica microtome.

Retina cross sections labeled with DAPI (Vector Laboratory Inc., Burlingame, Calif.) were used for morphometric analysis to evaluate outer nuclear layer (ONL) integrity/rod survival as described previously (Xu et al., 2012). In each hemisphere, the number of nuclei in the ONL and the thickness of the ONL were measured at 0.24 mm intervals in nine defined areas, starting at the optic nerve head and extending along the vertical meridian toward the dorsal and ventral ora serrata. The mean number of nuclei and ONL thickness at the dorsal and ventral locations was then calculated. In each experimental group, two-three sections from each of the retinas of three-four mice were measured. The averages of the measurements in each location were plotted, and the measurements in each hemisphere were analyzed and graphed using GraphPad Prism software (GraphPad Software, San Diego, Calif.).

Immunohistochemical labeling of cones using antibodies against peanut agglutinin (PNA), cone opsin, cone arrestin (CAR), and guanine nucleotide-binding protein G(t) subunit alpha-2 (GNAT2) was performed as described previously (Ding et al., 2009). Briefly, retinal whole mounts or sections were blocked in Hank's balanced salt solution containing 5% bovine serum albumin (BSA) and 0.5% Triton-X 100 for 1 hour at room temperature. Primary antibody incubation (anti-M-opsin, 1:500; anti-S-opsin, 1:500; anti-CAR, 1:500; and anti-GNAT2, 1:500) was performed at room temperature for 1 hour. Following ALEXA FLUOR®-488 or -568 (Molecular Probes, Inc., Eugene, Oreg.) or FITC-conjugated secondary antibody incubation and rinses, slides were mounted and cover-slipped. PNA immunohistochemistry was performed using biotinylated PNA (1:50) and streptavidin-FITC (1:200). Fluorescent signals were imaged using an Olympus AX70 fluorescence microscope (Olympus Corp., Center Valley, Pa.) with QCapture imaging software (QImaging Corp., Surrey, BC, Canada) or an Olympus IX81-FV500 confocal laser scanning microscope (Olympus, Melville, N.Y.) (using excitation wavelengths of 543 nm for ALEXA FLUOR®-568 and 488 nm for FITC) and FLUOVIEW® imaging software (Olympus, Melville, N.Y.). Evaluation of cone density on retinal whole mounts and retinal cross-sections was performed as described previously (Xu et al., 2011; and Komeima et al., 2006). For retinal whole mounts, images were taken using a 40× objective on an Olympus microscope, approximately 1.0 mm from the optic nerve in the center of each quadrant (FIG. 1). Image scale was calibrated and cones were counted in four regions, each with dimensions of 317 μm×317 μm, using ImageJ software (ImageJ software website from National Institutes of Health, Bethesda, Md.). Cone density on retinal cross section was evaluated by counting the number of cones present in the dorsal and ventral areas. The averages of the counts were analyzed and graphed using GraphPad Prism software (GraphPad Software, San Diego, Calif.).

Retinal Membrane Preparation, SDS-PAGE, and Western Blot Analysis.

Protein SDS-PAGE and Western blotting were performed as described previously (Ding et al., 2009). Briefly, retinas were homogenized in homogenization buffer [20 mM HEPES-NaOH, pH 7.4, 1 mM EDTA, 200 mM sucrose, containing protease mixture (Roche Applied Science, Indianapolis, Ind.)]. The nuclei and cell debris were removed from the homogenate by centrifugation at 1,000×g for 10 min at 4° C. The resulting supernatant was centrifuged at 16,000×g for 30 min at 4° C. The resultant membranes (pellet fraction) were used in Western blot analysis.

Retinal membrane proteins were subjected to SDS-PAGE and transferred onto polyvinylidene difluoride membranes. Following one hour of blocking in 5% nonfat milk in Tris-buffered saline (TBS) (wt/vol) at room temperature, blots were incubated with primary antibody (anti-S-opsin, 1:2,000; anti-M-opsin, 1:2,000; anti-GNAT2, 1:1,500; anti-CAR, 1:2,000; or anti-actin, 1:5,000) overnight at 4° C. After rinsing in TBS with 0.1% Tween 20, blots were incubated with HRP-conjugated secondary antibodies (at 1:15,000 for anti-actin; 1:25,000 for other antibodies) for 1 hour at room temperature. SUPERSIGNAL® West Dura Extended Duration chemiluminescent substrate (Pierce Biotechnology Inc., Rockford, Ill.) was used to detect binding of the primary antibodies to their cognate antigens. Images were captured using a Kodak Image Station 4000R Digital Imaging System (Carestream Molecular Imaging, New Haven, Conn.) and densitometric quantification was performed using Kodak Molecular Imaging software.

Quantitative (q)-RT-PCR.

Total RNA preparation and reverse transcription was performed as described previously (Ma et al., 2013). qRT-PCR was performed to detect mRNA levels of S-opsin and M-opsin in retinal isomerase RPE65 deficient (Rpe65$^{-/-}$) and cone photoreceptor function loss type 1 (cpfl1) mice following anti-thyroid treatment. The mouse hypoxanthine guanine phosphoribosyl transferase 1 (HPRT-1) was included as an internal control. Primers were as follows:

```
S-opsin Forward:
                                  (SEQ ID NO: 1)
5'-TGAAAGAGTGGGAAAGGATGG;

S-opsin Reverse:
                                  (SEQ ID NO: 2)
5'-CACCAAGACAGAAAGAGTAGGG;

M-opsin Forward:
                                  (SEQ ID NO: 3)
5'-GCTACTTCGTTCTGGGACAC;

M-opsin Reverse:
                                  (SEQ ID NO: 4)
5'-CAAATCTCACATTGCCAAAGGG;

HPRT-1 Forward:
                                  (SEQ ID NO: 5)
5'-GCAAACTTTGCTTTCCCTGG;
and HPRT-1 Reverse:
                                  (SEQ ID NO: 6)
5'-CAAGGGCATATCCAACAACA.
```

The qRT-PCR assays were performed using a real-time PCR detection system (iCycler; Bio-Rad Laboratories), and the relative gene expression value was calculated based on the ΔΔcT method as described previously (Ma et al., 2013).

Results of Example 1

Suppressing TH Signaling Preserves Cones in Rpe65$^{-/-}$ Mice.

Figure 2:
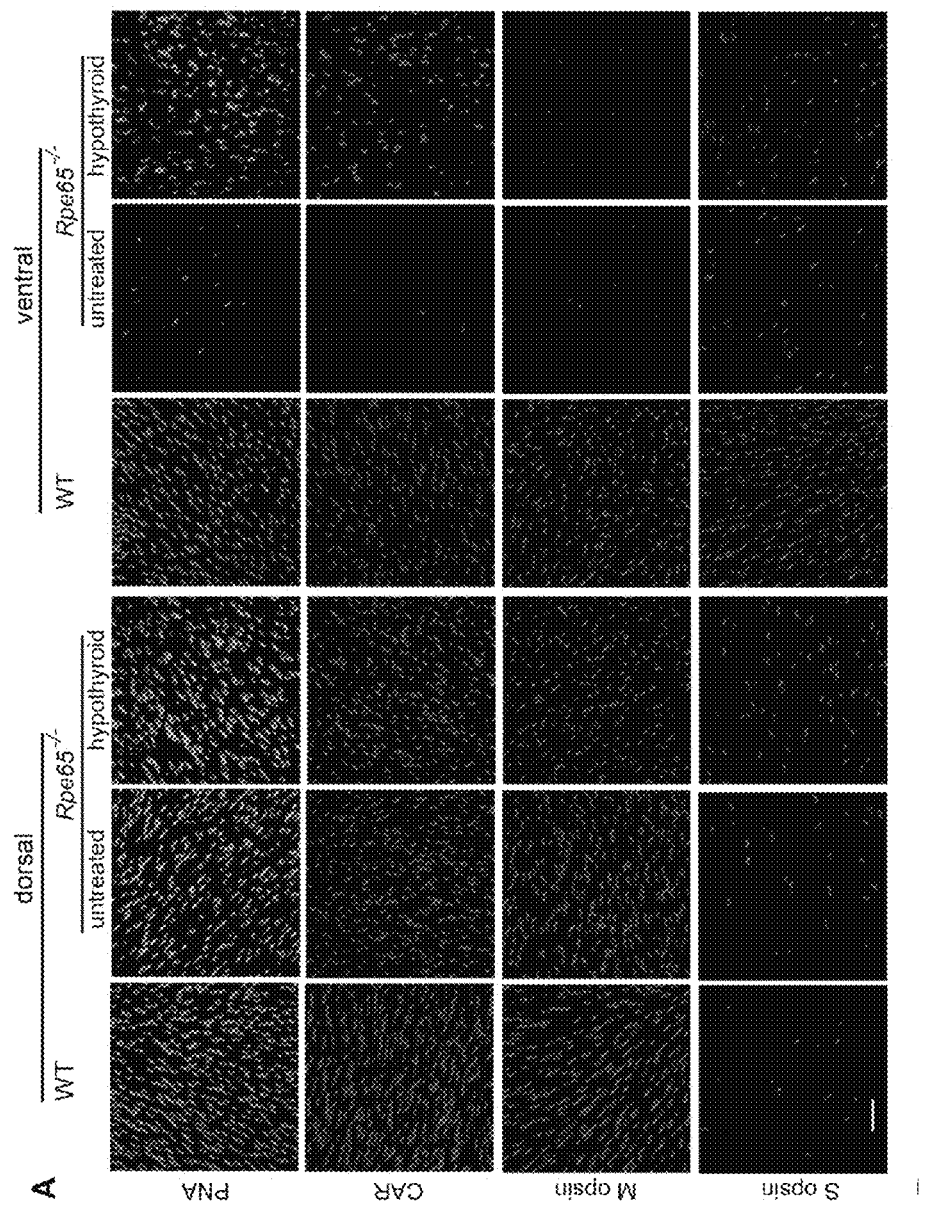
FIG. 2 illustrates that suppressing TH signaling preserved cones in Rpe65$^{-/-}$ mice. Rpe65$^{-/-}$ mice received anti-thyroid treatment for 30 days, beginning on postnatal day 1 (P1). At the end of the treatment, cone density was evaluated by immunofluorescence labeling on retinal whole mounts, and cone specific protein expression was evaluated by Western blotting. (A) Representative confocal images of immunofluorescence labeling of peanut agglutinin (PNA), cone arrestin (CAR), M-opsin, and S-opsin in hypothyroid and untreated Rpe65$^{-/-}$ mice and wild-type (WT) mice (Scale bar: 10 µm). (B) Correlating quantitative analysis of the immunofluorescence labeling. (C) Shown are representative images of the Western blot detection of CAR, guanine nucleotide-binding protein G(t) subunit alpha-2 (GNAT2), M-opsin, and S-opsin, and the correlating quantifications. Data are represented as mean±SEM of three to four assays using eyes/retinas from four mice. Unpaired Student/test was used to determine significance between hypothyroid and untreated Rpe65$^{-/-}$ mice (* $P<0.05$,  $P<0.01$, and * $P<0.001$).
Figure 2:
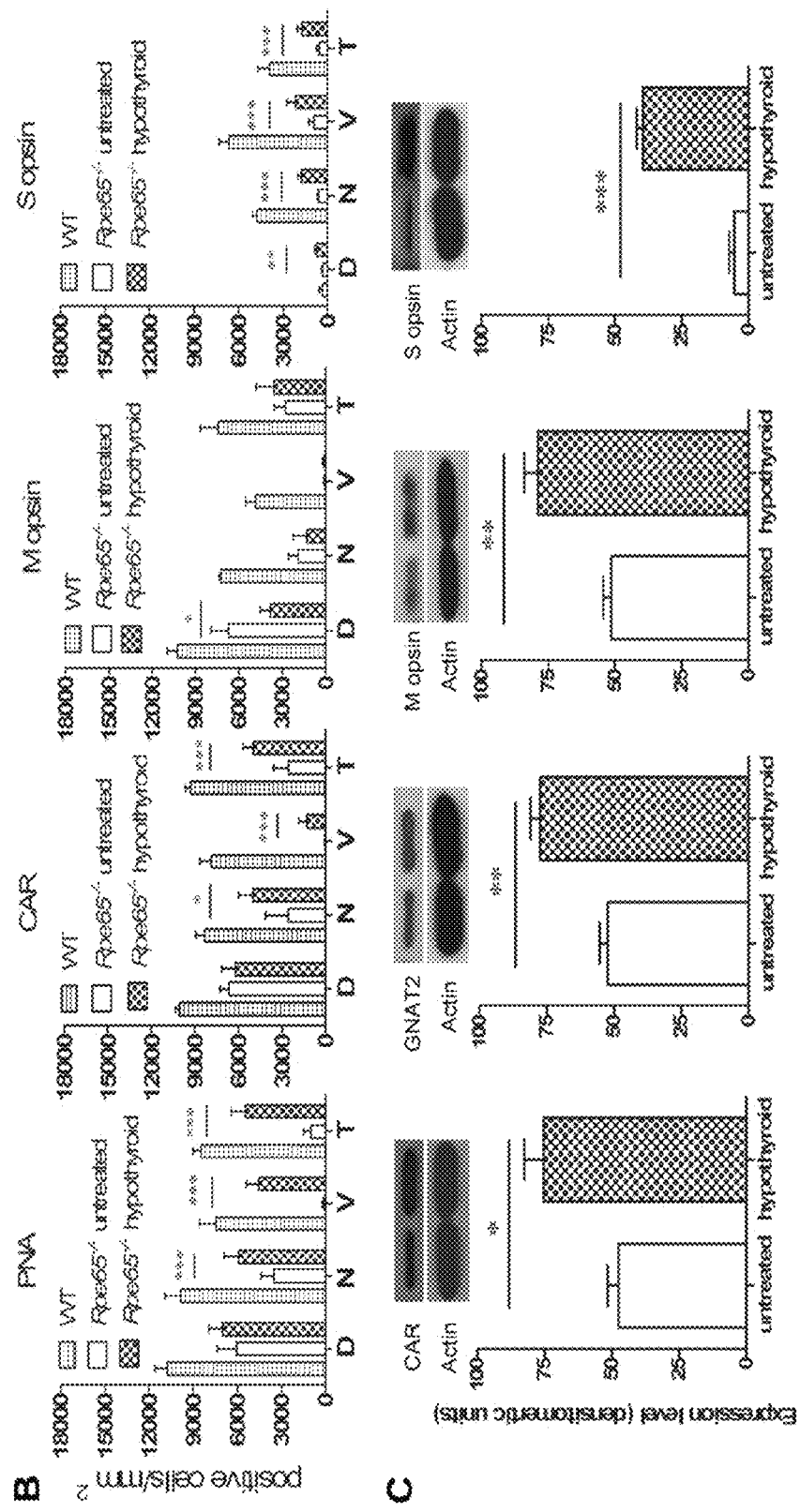
Figure 3:
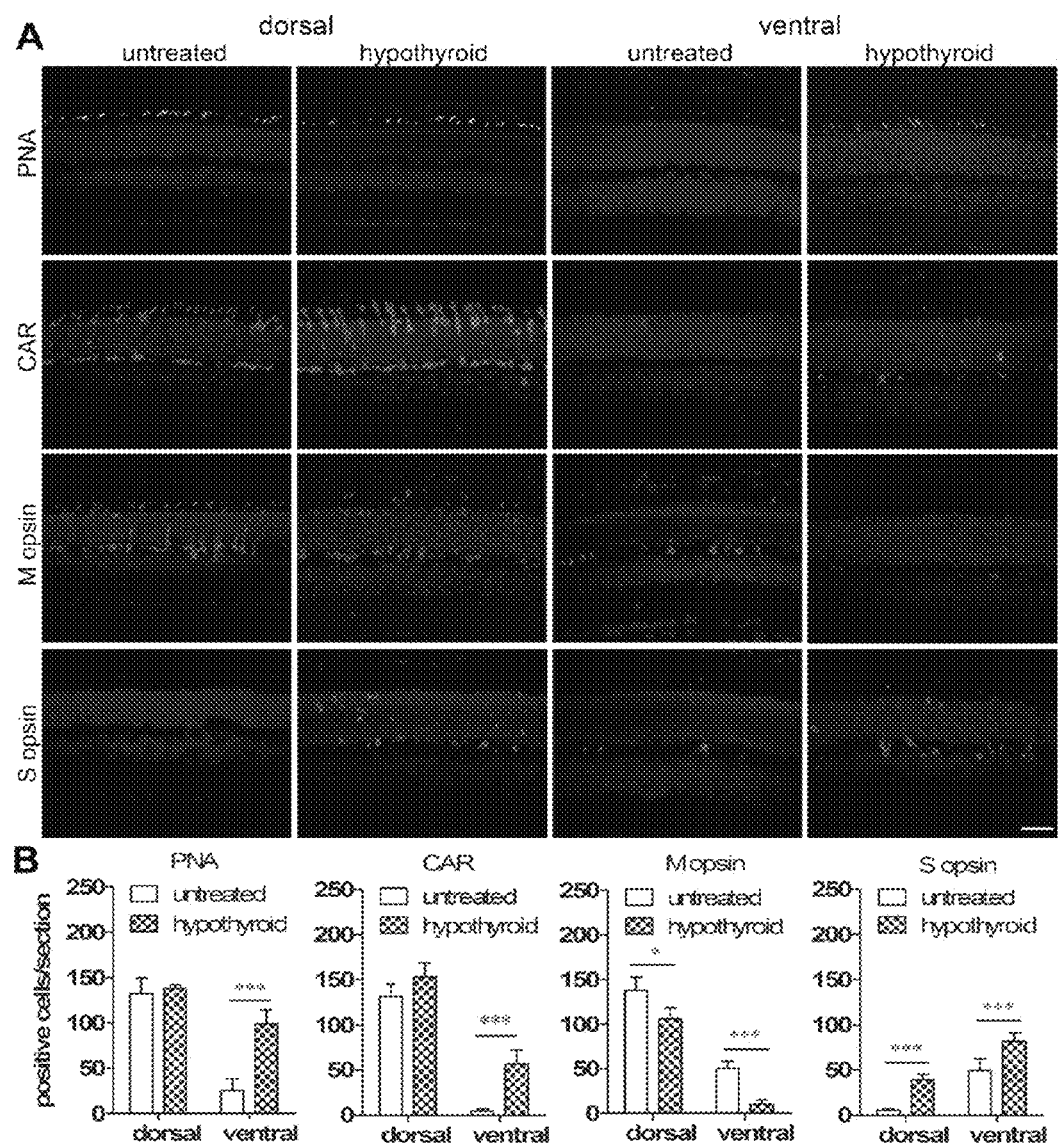
FIG. 3 illustrates that suppressing thyroid hormone (TH) signaling preserved cones in Rpe65$^{-/-}$ mice. Rpe65$^{-/-}$ mice received anti-thyroid treatment for 30 days, beginning on P1. At the end of the treatment, cone density was evaluated by immunofluorescence labeling of PNA, CAR, M-opsin, and 5-opsin on retinal cross sections. (A) Representative confocal images of the immunofluorescence labeling in hypothyroid and untreated Rpe65$^{-/-}$ mice (Scale bar: 50 µm). (B) Correlating quantitative analysis of the immunofluorescence labeling. Data are represented as mean±SEM of three to four assays using eyes from four mice. Unpaired Student t test was used to determine significance between hypothyroid and untreated mice (* $P<0.05$ and *** $P<0.001$).

Rpe65$^{-/-}$, a severe cone degeneration model, displays rapid ventral and central cone loss, whereas dorsal cones are preserved relatively well. The cone density evaluation by peanut agglutinin (PNA) and cone arrestin (CAR) labeling in Rpe65$^{-/-}$ mice showed a degeneration pattern similar to that reported previously, i.e., the ventral and central retina shows early onset, fast cone degeneration (about 10% of the wild-type level remained at postnatal day 30, P30), whereas the peripheral dorsal retina degenerated more slowly (about 50% of the wild-type level remained at P30) (FIG. 2A-B). Rpe65$^{-/-}$ mice received anti-thyroid drug (methimazole (MMI) and sodium perchlorate monohydrate (PM)) treatment for 30 days, beginning on P1. The anti-thyroid treatment reduced serum T3 levels by about 30% in the treated mice, compared with untreated controls, when measured on the last day of the treatment (Table 1). This treatment significantly increased cone density. Cone density evaluation showed that the number of PNA-labeled cones in the ventral and dorsal retinas in anti-thyroid treated Rpe65$^{-/-}$ mice increased about 6- and 1.3-fold, respectively, compared with untreated controls (FIG. 2A-B). Similarly, CAR-labeled cones in the ventral retinas increased about 4-fold. The increased cone density in anti-thyroid treated Rpe65$^{-/-}$ mice was also shown by PNA and CAR labeling on retinal cross sections as shown in FIG. 3. These results demonstrate a protective role of suppressing TH signaling in Rpe65$^{-/-}$ cones.

TABLE 1

Serum T3 levels (nM) in anti-thyroid- or T3-treated mice

| Mouse lines | Untreated | Anti-thyroid treated | T3 treated |
|---|---|---|---|
| Cpfl1 | 0.76 ± 0.09 | 0.39 ± 0.02** | |
| Rpe65$^{-/-}$ | 0.71 ± 0.03 | 0.51 ± 0.02** | |
| Cngb3$^{-/-}$ | 0.46 ± 0.03 | | 3.85 ± 0.55** |
| Gucy2e$^{-/-}$ | 0.62 ± 0.04 | | 3.43 ± 0.48*** |

**p < 0.01,
***p < 0.001

Figure 4:
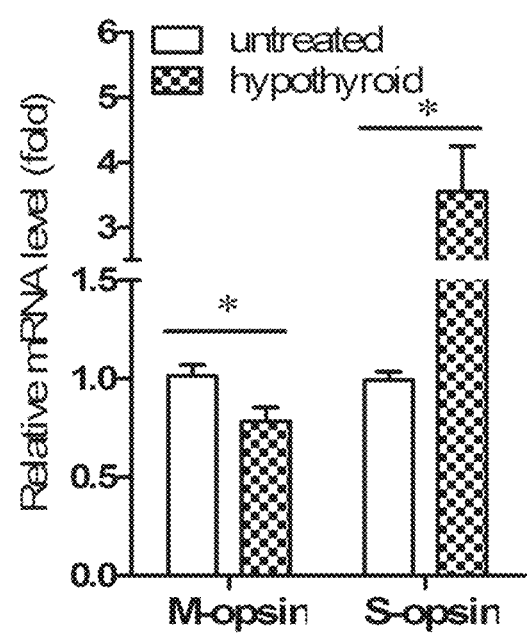
FIG. 4 illustrates that suppressing TH signaling increased the mRNA level of S-opsin and reduced the mRNA level of M-opsin in Rpe65$^{-/-}$ mice. Rpe65$^{-/-}$ mice received anti-thyroid treatment for 30 days, beginning on P1. At the end of the treatment, retinas were isolated and analyzed for mRNA levels of S-opsin and M-opsin by qRT-PCR. Data are represented as mean±SEM of three assays using retinas from four mice. Unpaired Student t test was used to determine significance between hypothyroid and untreated mice (* P<0.05).

The effect of TH signaling on cone opsin expression has been well characterized. In this Example, M- and S-cone density was examined by labeling M- and S-opsin with specific antibodies. In agreement with reported information in wild-type mice, M-opsin-labeled cones (M cones) were significantly reduced in Rpe65$^{-/-}$ mice following anti-thyroid treatment, whereas S-opsin-labeled cones (S cones) were greatly increased, compared with untreated controls (FIGS. 2A-B and 3). Cone preservation in Rpe65$^{-/-}$ mice following TH signaling suppression was also evaluated by examining the expression levels of cone specific proteins. CAR and cone transducin α-subunit [guanine nucleotide-binding protein G(t) subunit alpha-2 (GNAT2)] expression levels in anti-thyroid treated Rpe65$^{-/-}$ mice increased by 30-40%, compared with untreated controls (FIG. 2C). Similar to S-opsin labeling of cones, S-opsin expression levels were increased about 5-fold. By quantitative RT-PCR (qRT-PCR), the mRNA levels of S-opsin and M-opsin in anti-thyroid-treated Rpe65$^{-/-}$ mice increased about 3.8-fold and decreased by about 20%, respectively (FIG. 4). This finding is consistent with the previously demonstrated effect of TH signaling on cone opsin expression.

Suppressing TH Signaling Preserves Cones in Cpfl1 Mice.

Figure 5:
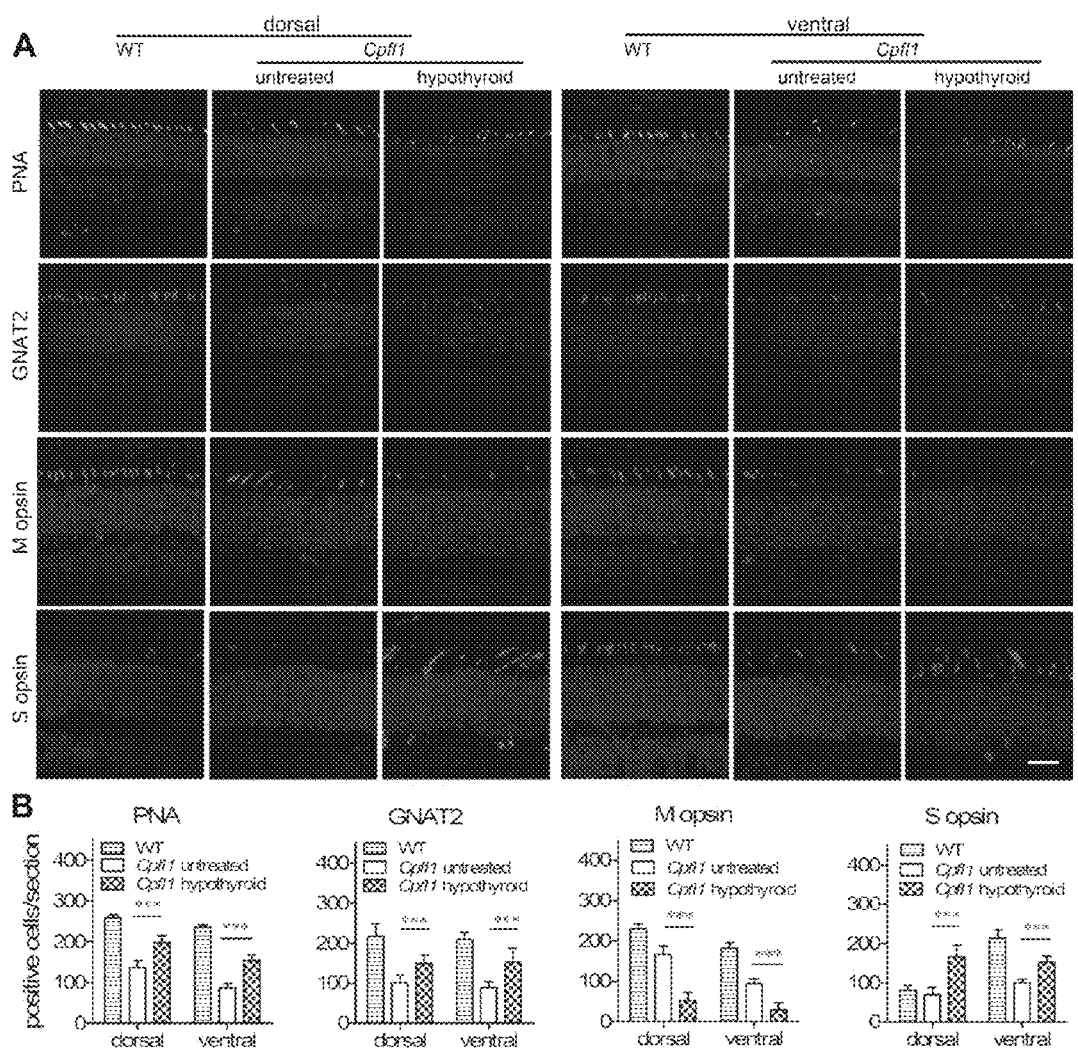
FIG. 5 illustrates that suppressing TH signaling preserved cones in cpfl1 mice. Cpfl1 mice received anti-thyroid treatment for 30 days, beginning on P1. At the end of the treatment, cone density was evaluated by immunofluorescence labeling on retinal cross sections. (A) Representative confocal images of immunofluorescence labeling of PNA, GNAT, M-opsin, and 5-opsin in hypothyroid and untreated cpfl1 mice and wild-type (WT) mice (Scale bar: 50 μm). (B) Correlating quantitative analysis of the immunofluorescence labeling. Data are represented as mean±SEM of four assays using eyes from three to four mice. Unpaired Student t test was used to determine significance between hypothyroid and untreated mice *** P<0.001).
Figure 6:
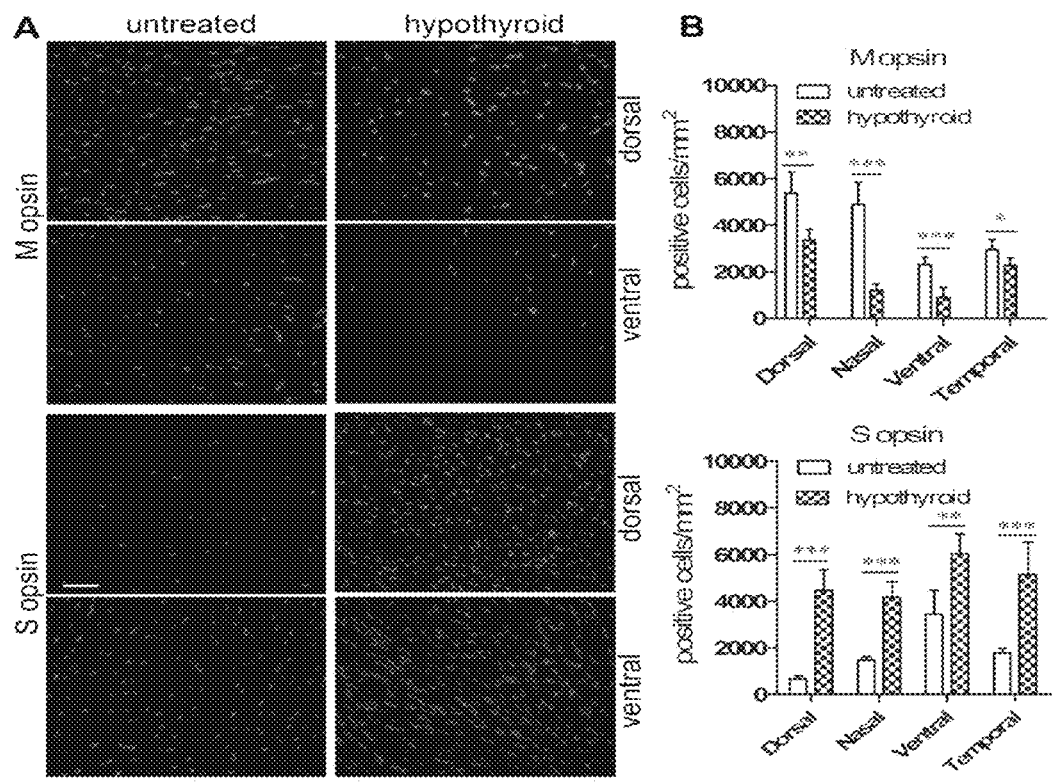
FIG. 6 illustrates that suppressing TH signaling reduced expression of M-opsin and increased expression of 5-opsin in cpfl1 mice. Cpfl1 mice received anti-thyroid treatment for 30 days, beginning on P1. At the end of the treatment, cone density was evaluated by immunofluorescence labeling on retinal whole mounts. (A) Representative confocal images of immunofluorescence labeling of M-opsin and S-opsin in hypothyroid and untreated cpfl1 mice (Scale bar: 10 μm). (B) Correlating quantitative analysis of the immunofluorescence labeling. Data are represented as mean SEM of four assays using eyes from three to four mice. Unpaired Student t test was used to determine significance between hypothyroid and untreated mice (* P<0.05,  P<0.01 and * P<0.001).
Figure 7:
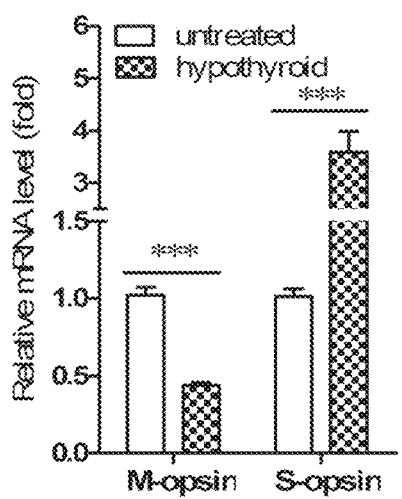
FIG. 7 illustrates that suppressing TH signaling increased the mRNA level of S-opsin and reduced the mRNA level of M-opsin in cpfl1 mice. Cpfl1 mice received anti-thyroid treatment for 30 days, beginning on P1. At the end of the treatment, retinas were isolated and analyzed for mRNA levels of S-opsin and M-opsin by qRT-PCR. Data are represented as mean d-=SEM of three assays using retinas from four mice. Unpaired Student t test was used to determine significance between hypothyroid and untreated cpfl1 mice (*** P<0.001).

Cpfl1, a naturally occurring cone degeneration mouse line, is another fast and severe cone degeneration model. Cpfl1 mice received anti-thyroid drug (MMI and PM) treatment for 30 days, beginning on P1. The anti-thyroid treatment reduced serum T3 levels in the treated mice by about 50%, compared with untreated controls, when measured on the last day of the treatment (Table 1). This treatment significantly improved cone survival. FIG. 5 shows representative images of PNA, GNAT2, M-opsin and S-opsin labeling of retinal cross sections (FIG. 5A) and their quantifications (FIG. 5B) in P30 anti-thyroid treated and untreated cpfl1 mice. Cone density in cpfl1 mice was about 50% of the wild-type level. Following anti-thyroid treatment, cone density was increased to about 70-80% of the wild-type level (FIG. 5A-B). Similar to the observations in Rpe65$^{-/-}$ mice, M cones were significantly reduced, whereas S cones were greatly increased (about a 0.7- to 5.0-fold increase, depending on the retinal areas, with the maximal increase observed in the dorsal retina) (FIGS. 5 and 6). qRT-PCR analysis showed a 3.8-fold increase in S-opsin mRNA levels and a 50% decrease of M-opsin mRNA level in cpfl1 mice after anti-thyroid treatment (FIG. 7).

Figure 8:
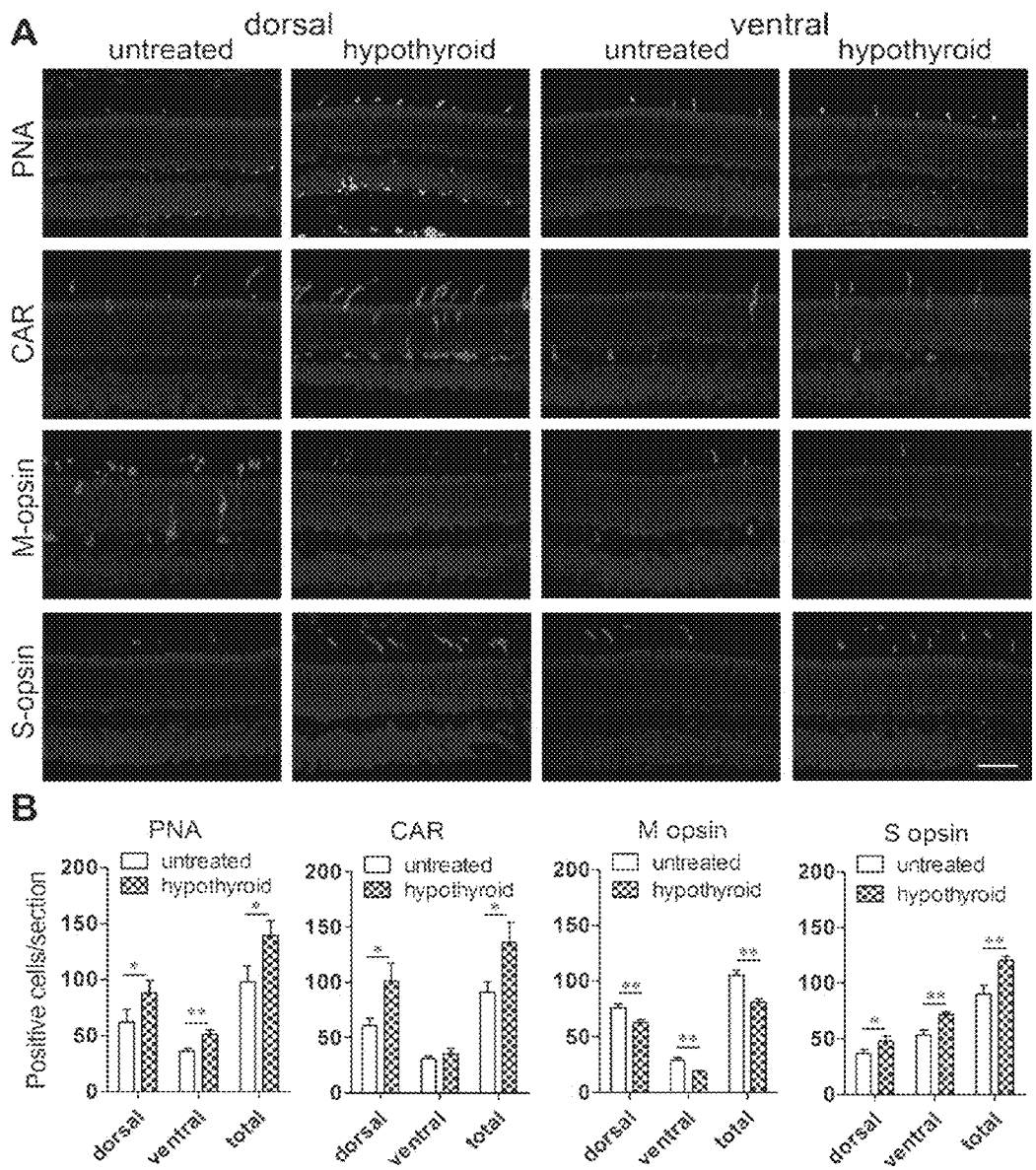
FIG. 8 illustrates that suppressing TH signaling preserved cones in cpfl1 mice with treatment starting after weaning. Cpfl1 mice received anti-thyroid treatment for 30 days, beginning on P25. At the end of the treatment, cone density was evaluated by immunofluorescence labeling on retinal sections. (A) Representative confocal images of immunofluorescence labeling of PNA, CAR, M-opsin, and S-opsin in hypothyroid and untreated mice (Scale bar: 50 μm). (B) Correlating quantitative analysis of the immunofluorescence labeling. Data are represented as mean±SEM of three assays using eyes from four mice. Unpaired Student t test was used to determine significance between hypothyroid and untreated cpfl1 mice (* P<0.05 and ** P<0.01).
Figure 9:
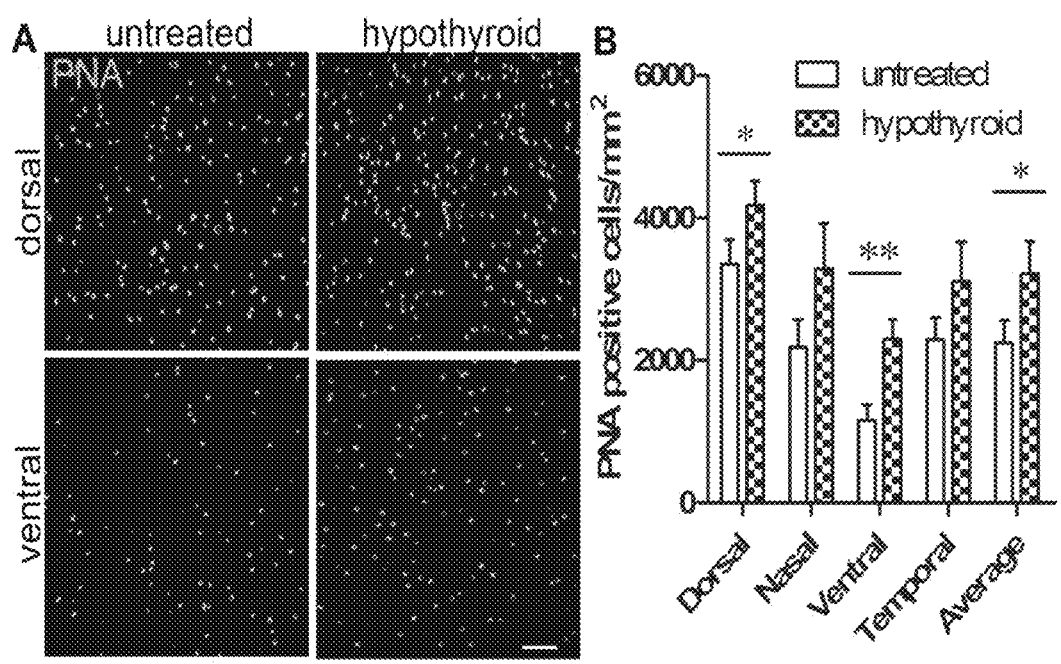
FIG. 9 illustrates that suppressing TH signaling preserved cones in cpfl1 mice with treatment starting after weaning. Cpfl1 mice received anti-thyroid treatment for 30 days, starting from P25. At the end of the treatment, cone density was evaluated by immunofluorescence labeling on retinal whole mounts. (A) Representative confocal images of immunofluorescence labeling of PNA in hypothyroid and untreated cpfl1 mice (Scale bar: 10 μm). (B) Correlating quantitative analysis of the immunofluorescence labeling. Data are represented as mean±SEM of three to four assays using eyes from four mice. Unpaired Student t test was used to determine significance between hypothyroid and untreated cpfl1 mice (* P<0.05 and ** P<001).

To determine whether suppressing TH signaling affects post-mitotic cone survival, adult cpfl1 mice were treated with anti-thyroid drugs beginning on P25 and continuing for 30 days. Cone density analysis revealed that PNA- and CAR-labeled cones on retinal sections prepared from treated cpfl1 mice increased about 30-40%, compared with age-matched, untreated controls (FIG. 8). The improved cone survival was also confirmed by PNA labeling on retinal whole mounts (FIG. 9). Similar to the observation obtained in mice receiving treatment at an early age (FIGS. 5 and 6), M cones were significantly reduced, whereas S cones were greatly increased (FIG. 8). These results indicate that suppressing TH signaling after retina development is completed still preserves cones.

Stimulating TH Signaling Deteriorates Cones in Cngb3$^{-/-}$ Mice.

Figure 10:
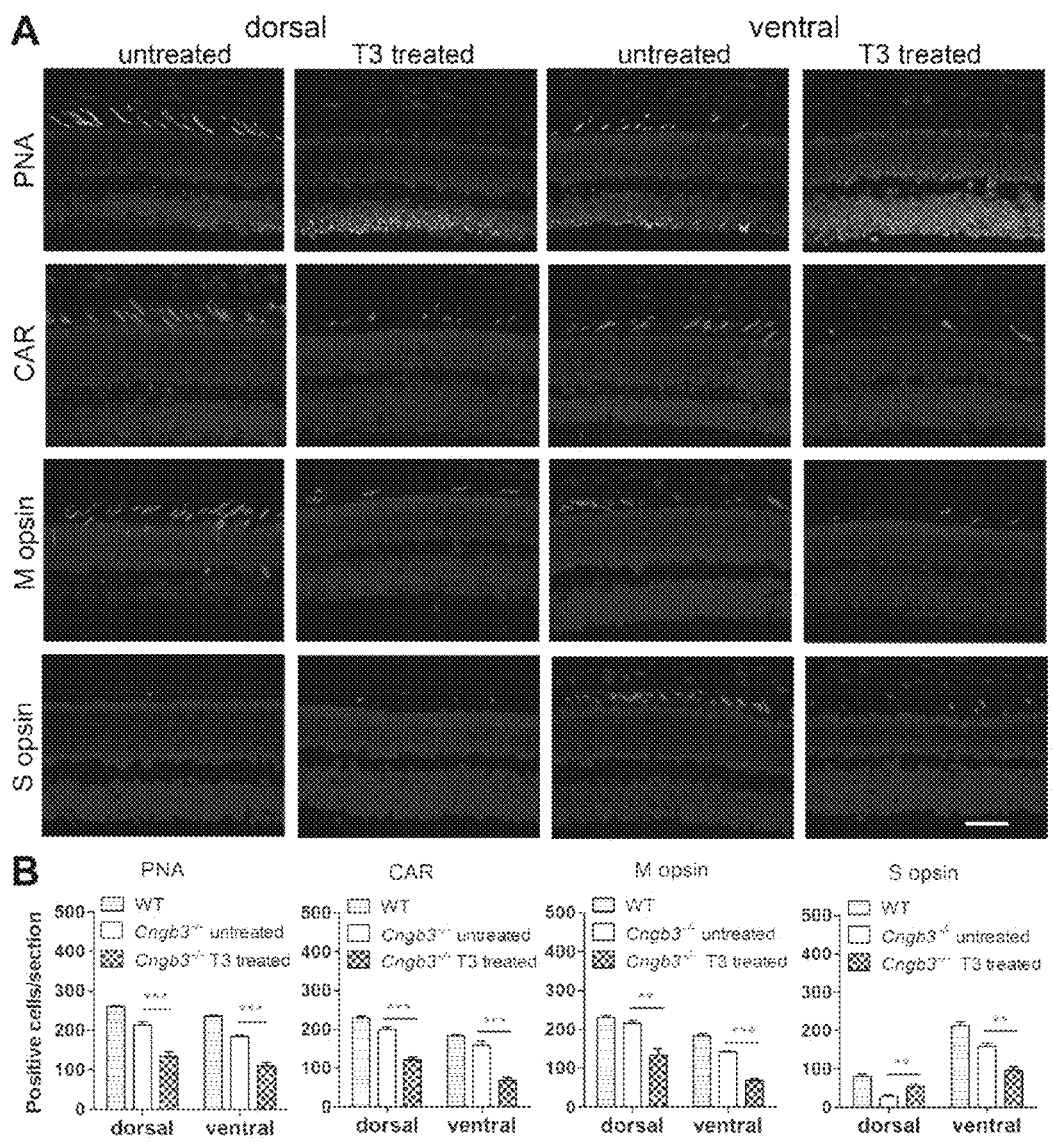
FIG. 10 illustrates that stimulating TH signaling deteriorated cones in cyclic nucleotide-gated channel B subunit deficient (Cngb3$^{-/-}$) mice. Cngb3$^{-/-}$ mice received triiodothyronine (T3) treatment for 30 days; beginning on P1. At the end of the treatment, cone density was evaluated by immunofluorescence labeling on retinal sections. (A) Representative confocal images of immunofluorescence labeling of PNA, CAR, M-opsin, and 5-opsin in T3-treated and untreated Cngb3$^{-/-}$ mice (Scale bar: 50 μm). (B) Correlating quantitative analysis of the immunofluorescence labeling. Data are represented as mean±SEM of three to four assays using eyes from four mice. Unpaired Student t test was used to determine significance between T3-treated and untreated Cngb3$^{-/-}$ mice ( P<0.01 and * P<0.001).
Figure 11:
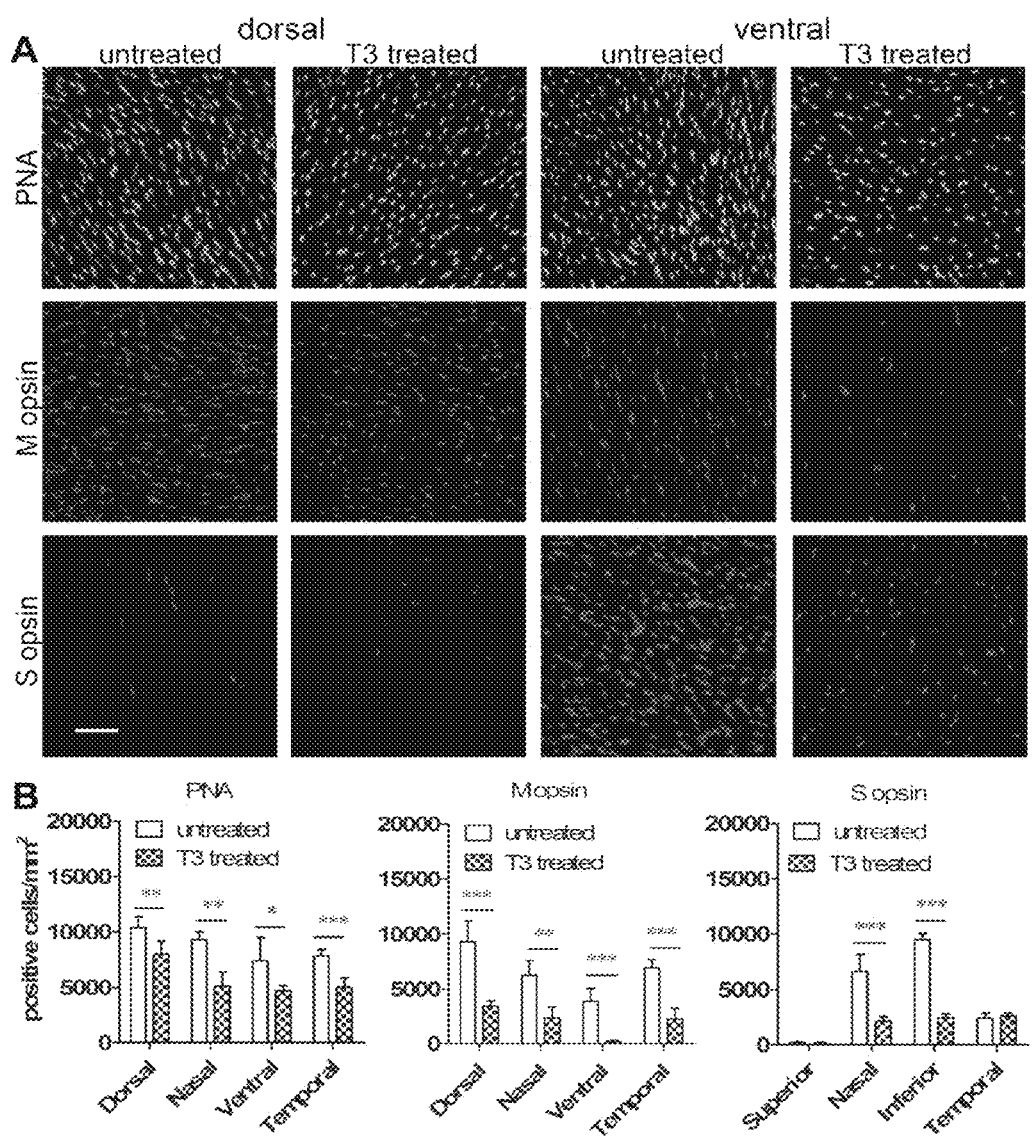
FIG. 11 illustrates that stimulating TH signaling deteriorated cones in Cngb3$^{-/-}$ mice. Cngb3$^{-/-}$ mice received T3 treatment for 30 days, beginning on P1. At the end of the treatment, cone density was evaluated by immunofluorescence labeling on retinal whole mounts. (A) Representative confocal images of immunofluorescence labeling of PNA, M-opsin, and S-opsin in T3-treated and untreated Cngb3$^{-/-}$ mice (Scale bar: 10 μm). (6B) Correlating quantitative analysis of the immunofluorescence labeling. Data are represented as mean±SEM of three to four assays using eyes from four mice. Unpaired Student t test was used to determine significance between T3-treated and untreated mice (* P<0.05,  P<0.01, and * P<0.001).

Cngb3$^{-/-}$ mice, which show a slow progressive and moderate cone degeneration phenotype, were used to determine the effect of stimulating TH signaling with T3. Cngb3$^{-/-}$ mice received T3 treatment (0.1 μg/g body weight, subcutaneous (s.c.) injection, once each day) for 30 days, beginning on P1. The treatment increased serum T3 levels in the treated mice by about 8-fold, compared with untreated controls, when measured around 24 hours after the last injection (Table 1). Following T3 treatment, cone density in Cngb3$^{-/-}$ mice was significantly reduced. PNA-labeled cones in the T3-treated mice were reduced by about 30%, and CAR-labeled cones by about 40%, compared with untreated Cngb3$^{-/-}$ mice (FIGS. 10 and 11). These results demonstrate that stimulating TH signaling deteriorates cones. In agreement with the findings in wild-type mice, M- and S-opsin labeled-cones in T3-treated Cngb3$^{-/-}$ mice were greatly reduced, compared with untreated controls (FIGS. 10 and 11).

Stimulating TH Signaling Deteriorates Cones in Gucy2e$^{-/-}$ Mice.

Figure 12:
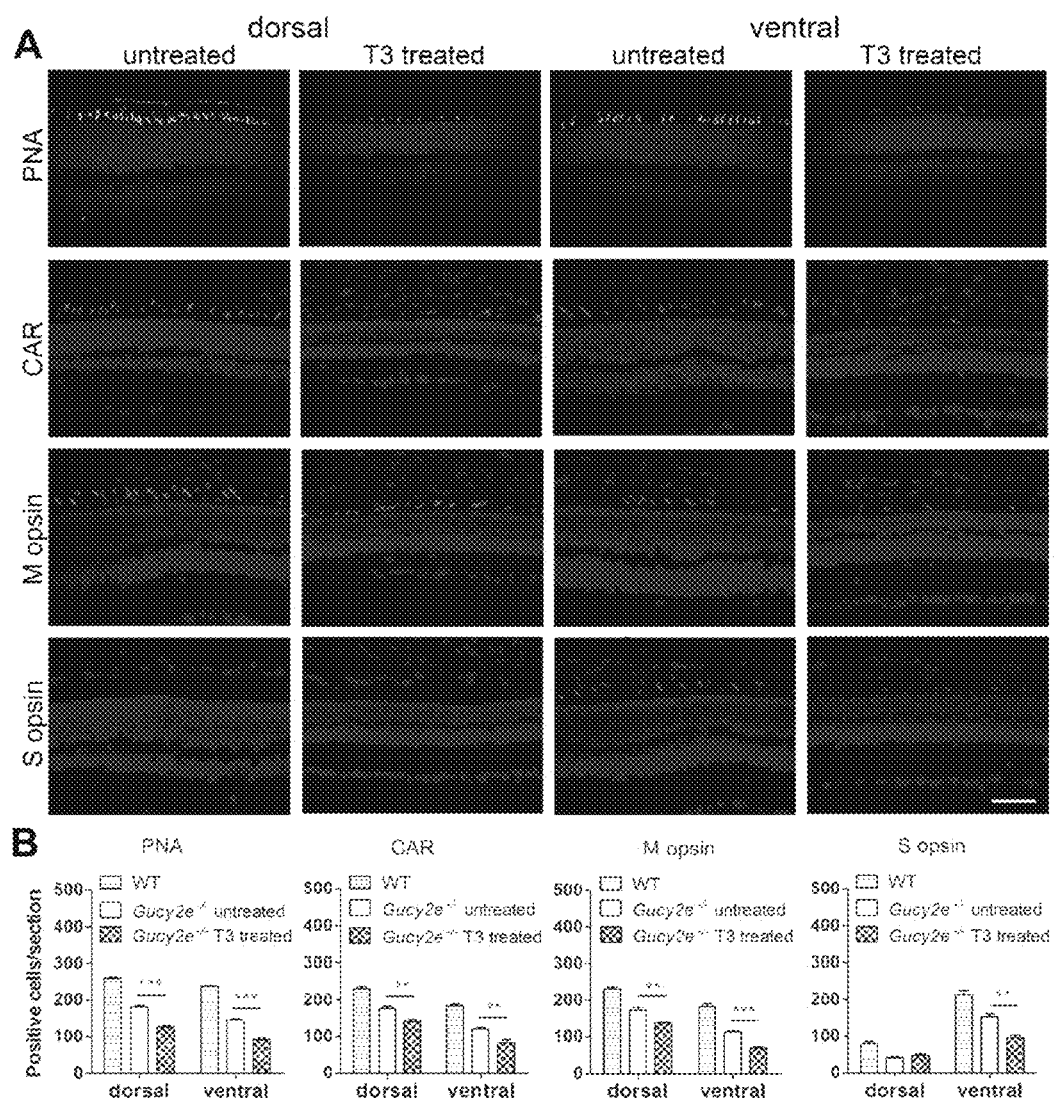
FIG. 12 illustrates that stimulating TH signaling deteriorated cones in guanylate cyclase 2e-deficient (Gucy2e$^{-/-}$)$^-$ mice. Gucy2e$^{-/-}$ mice received T3 treatment for 30 days, beginning on P1. At the end of the treatment, cone density was evaluated by immunofluorescence labeling on retinal sections. (A) Representative confocal images of immunofluorescence labeling of PNA, CAR, M-opsin, and S-opsin in T3-treated and untreated Gucy2e$^{-/-}$ mice (Scale bar: 50 μm). (B) Correlating quantitative analysis of the immunofluorescence labeling. Data are represented as mean±SEM of three to four assays using eyes from four mice. Unpaired Student t test was used to determine significance between T3-treated and untreated Gucy2e$^{-/-}$ mice ( p<0.01 and * p<0.001).

The Gucy2e$^{-/-}$ mouse line, a model with relatively slow progressive and moderate cone degeneration, was also used to determine the effect of stimulating TH signaling on cone survival. Gucy2e$^{-/-}$ mice received T3 treatment (0.1 μg/g body weight, subcutaneous injection, once each day) for 30 days, beginning on P1. The treatment increased serum T3 levels in the treated mice by about 6-fold, compared with untreated controls, when measured around 24 hours after the last injection (Table 1). Similar to the observation in Cngb3$^{-/-}$ mice, stimulating TH signaling significantly diminished cone density in Gucy2e$^{-/-}$ mice. Density of cones labeled by PNA, CAR, and cone opsin in T3-treated mice was reduced by about 30% compared with untreated controls (FIG. 12).

Effects of TH Signaling on Rod Photoreceptor Viability.

Figure 13:
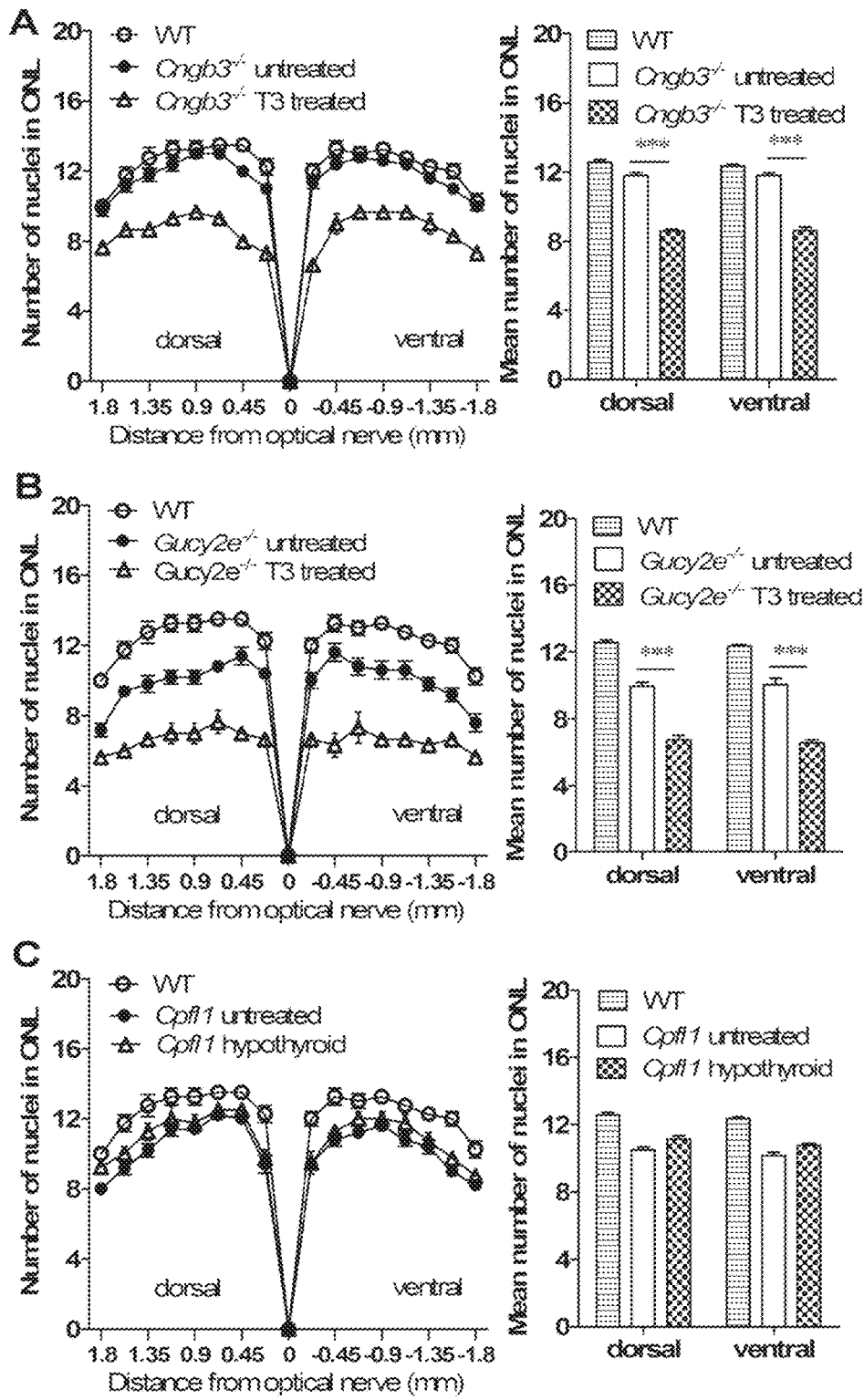
FIG. 13 illustrates the effects of TH signaling on rod photoreceptor viability. (A-B) Stimulating TH signaling caused rod degeneration in Cngb3$^{-/-}$ (A) and Gucy2e$^{-/-}$ (B) mice. Mice received T3 treatment for 30 days, beginning on P1. At the end of the treatment, retinal morphometric analysis was performed on retinal cross sections. (C) Suppressing TH signaling does not affect rod viability in cpfl1 mice. Cpfl1 mice received anti-thyroid treatment for 30 days, beginning on P1. At the end of the treatment, retinal morphometric analysis was performed on retinal cross sections. Shown are results of the nuclei count in the outer nuclear layer (ONL) (left panels) and the mean numbers of nuclei in the ONL in the dorsal and ventral regions (right panels). Data are represented as mean±SEM of three to four assays using eyes from four mice. Unpaired Student t test was used to determine significance between treated and untreated mice (*** P<0.001).
Figure 14:
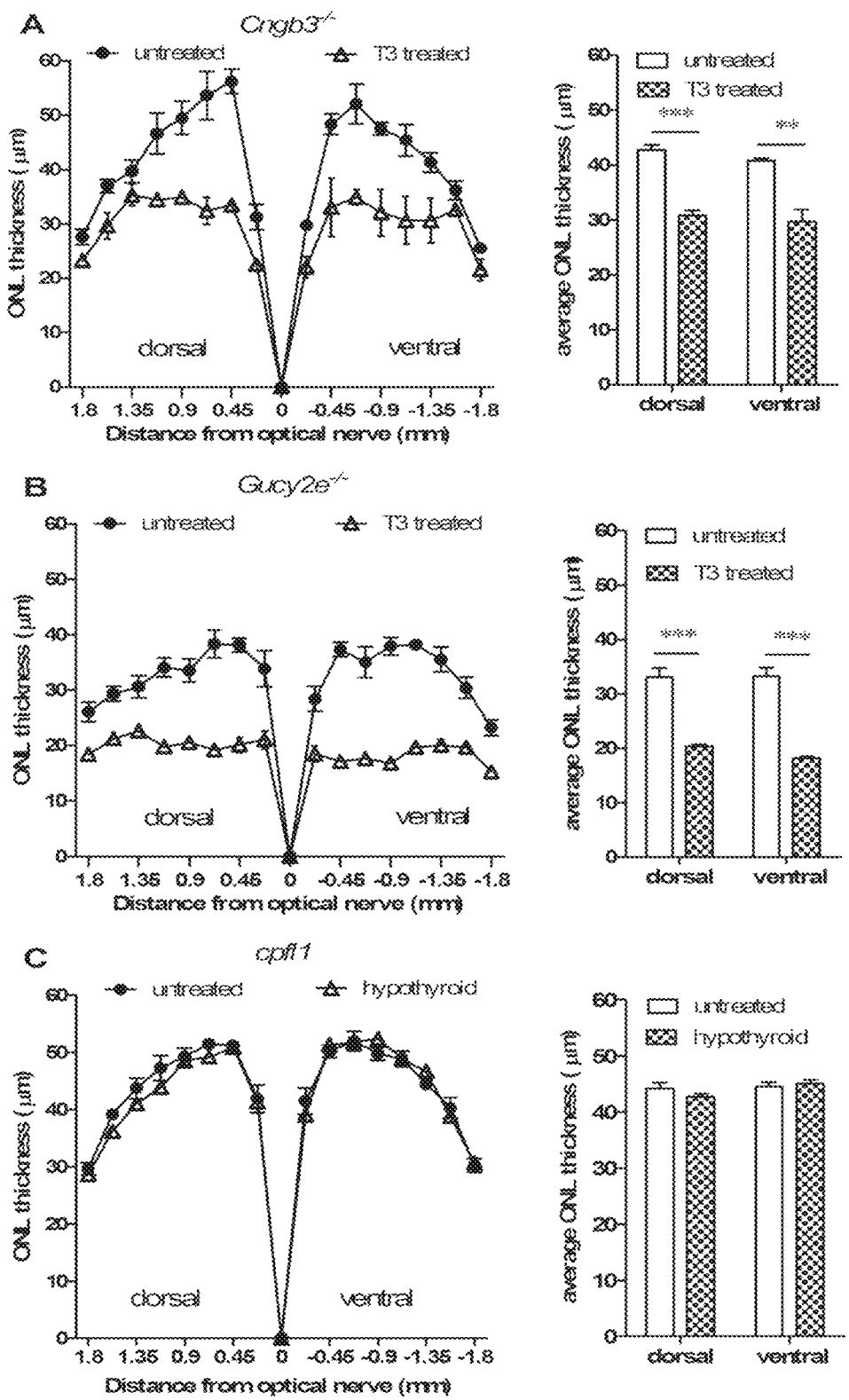
FIG. 14 illustrates the effects of TH signaling on rod photoreceptor viability. (A and B): Stimulating TH signaling causes rod degeneration in Cngb3$^{-/-}$ (A) and Gucy2e$^{-/-}$ (B) mice. Mice received T3 treatment for 30 days, beginning on P1. At the end of the treatment, retinal morphometric analysis was performed on retinal cross sections. (C) Suppressing TH signaling does not affect rod viability in cpfl1 mice. Cpfl1 mice received anti-thyroid treatment for 30 days starting from P1. At the end of the treatment, retinal morphometric analysis was performed on retinal cross sections. Shown are measurements of outer nuclear layer (ONL) thickness (left panels) and average ONL thickness in the dorsal and ventral regions (right panels). Data are represented as mean±SEM of three to four assays using eyes from four mice. Unpaired Student t test was used to determine significance between treated and untreated mice ( P<0.01 and * P<0.001).
Figure 15:
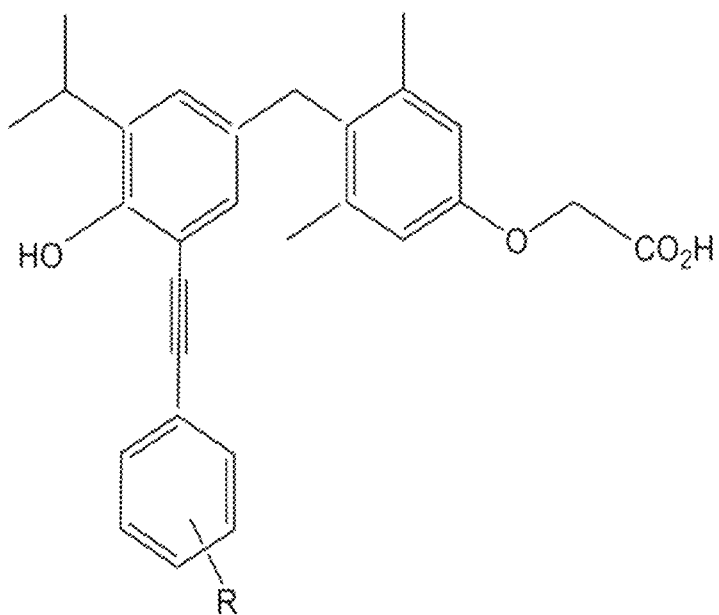
FIG. 15 represents a non-limiting example of a class of compounds that can be used as a TH receptor antagonist in accordance with some embodiments of the presently disclosed inventive concepts.

To determine whether stimulating TH signaling affects rod survival, retinal morphology and rod abundance were examined in Cngb3$^{-/-}$ and Gucy2e$^{-/-}$ mice that received T3 treatment for 30 days. The evaluation was performed by directly counting the number of nuclei in the outer nuclear layer (ONL) and by measuring ONL thickness. These methods are reasonably accurate measurements of photoreceptor layer integrity, and are commonly used to assess photoreceptor cell damage. Both measurements yielded the same results, showing T3 treatment impaired ONL integrity/rod survival in the experimental animals. The average number of nuclei in the ONL in Cngb3$^{-/-}$. (FIG. 13A) and Gucy2e$^{-/-}$ (FIG. 13B) mice was reduced by about 30%, compared with their respective untreated controls. Similar results were obtained with measurement of ONL thickness (FIG. 14). In a separate experiment, it was examined whether suppressing TH signaling has any negative effects on rod viability. The number of nuclei in the ONL and ONL thickness in anti-thyroid-treated cpfl1 mice was evaluated, and the results showed no differences between treated and untreated cpfl1 mice (FIGS. 13C and 14). Thus, unlike the effect of increased TH signaling, suppressing TH signaling does not have negative effects on rod photoreceptor viability.

Discussion of Example 1

As an essential growth regulator, TH plays a major role in cell proliferation, differentiation, and apoptosis. Using multiple mouse models, it has been demonstrated that suppressing TH signaling preserves cone photoreceptors in degenerating retinas. The protective effects were observed in both developing and postmitotic adult mice. Stimulating TH signaling, in contrast, promotes cone and rod photoreceptor death.

The effect of TH signaling on cone viability appears to be independent of its regulation of cone opsin expression. In the mouse retina, TH signaling plays a central role in cone opsin expression and the dorsal-ventral patterning. It increases expression of M-opsin, suppresses expression of S-opsin, and promotes/maintains their dorsal-ventral gradient distribution. The high expression level of S-opsin in the ventral retina has been associated with a more rapid degeneration in this region (compared with dorsal retina) that has been observed in retinal degeneration mouse models, including Rpe65$^{-/-}$ and Lrat$^{-/-}$ mice. It was shown that the rapid cone degeneration in Rpe65$^{-/-}$ and Lrat$^{-/-}$ mice is likely due to an absence of 11-cis-retinal, which causes aggregation of S-opsin and leads to apoptosis, and that the presence of a phenylalanine-rich region of S-opsin probably contributes to the protein aggregation.

The present Example has shown that suppressing TH signaling in Rpe65$^{-/-}$ and cpfl1 mice greatly reduced cone death, and was accompanied by increased expression of S-opsin and S cones and decreased M cones. Stimulating TH signaling in Cngb3$^{-/-}$ and Gucy2e$^{-/-}$ mice, in contrast, profoundly increased cone death, accompanied by reduced S-opsin expression level. Thus, without wishing to be bound by theory, TH signaling-mediated regulation of cone viability appears to be independent of TH regulation of cone opsin expression. This view is also supported by the following: (i) stimulating TH signaling induces death of rods, which do not express cone opsin; (ii) high TH signaling causes auditory deficits and cochlear degeneration (Ng et al., 2009); and (iii) high TH signaling induces death of other cell types, including cancer cells (Mihara et al., 1999; Sar et al., 2011; Yamada-Okabe et al., 2003; and Chiloeches et al., 2008), which do not express opsins.

Although TH signaling plays a major role in cone opsin expression and patterning, and high TH signaling induces cone and rod death, suppressing TH signaling has no negative effect on cone and rod structure, function (as evaluated by electroretinogram analysis), or survival during development and in adult mice (Ng et al., 2001; Lu et al., 2009; and Glaschke et al., 2010). This is in agreement with the observations in a human patient carrying TRβ2 mutations. This patient merely showed red/green color complications, but rod morphology and rhodopsin expression level remained normal (Weiss et al., 2012). In the present Example, no negative effect of anti-thyroid treatment on rod survival was found in the degenerating mouse models. The underlying mechanism in which high TH signaling becomes harmful for cones and rods remains to be determined, whereas low TH signaling is not detrimental, but protective.

TH signaling regulating cone viability is likely mediated via TRβ2, which, in the retina, is expressed only in cones (Applebury et al., 2007; and Ng et al., 2009). T3-induced cone death did not occur in Thrβ2$^{-/-}$ mice, and cone degeneration caused by deficiency of type 3 iodothyronine deiodinase (DIO3, an enzyme that inactivates T3) was rescued in Dio3$^{-/-}$/Thrβ2 mice (Ng et al., 2009). Recently, the receptor independent nongenomic mechanism, which does not include initial nuclear action of TH receptor or gene transcription, but involves the cell surface receptor and signal transduction pathway, has been implicated in TH signaling (Cheng et al., 2010; and Hiroi et al., 2006). Thus, the possibility that the receptor-independent nongenomic mechanism is also involved in TH signaling-regulated cone viability cannot be excluded.

Compared with the knowledge herein regarding the role of TH signaling and expression/function of TRβ2 in cones, the role of TH signaling in rods is not well defined. How rods die following T3 treatment is not well understood. Although TRα is more universally expressed, and its mRNA expression has been detected in the mouse eye (Ng et al., 2001), there is no firm evidence showing the role of TRα in mammalian photoreceptors. Thus, the mechanism of rod death following T3 treatment remains to be determined. Rod death might be associated with TRα, but it could equally likely involve the TRβ1 isoform (another product of the TRβ gene). In addition, there is a possibility that the loss of rods following T3 treatment is indirect, and a result of primary cone loss.

Understanding the TH signaling regulation of photoreceptor viability provides insights into cone preservation and therapeutic interventions. In accordance with the presently disclosed inventive concepts, as TRβ2 is expressed in cones only (in the retina), suppressing TH signaling locally can be used as a treatment to preserve cones in individuals experiencing retinal degeneration, or as a prophylactic treatment to enhance cone viability and/or reduce cone loss. For example, this can be accomplished using one or more pharmacological agents to inhibit TRβ2 binding and activation (such as described elsewhere herein, for example in Formulas (I)-(II) and FIGS. 15-24) or to genetically knock down TRβ2.

In addition, the impact of a local TH signaling inactivation has been observed in a variety of pathophysiological conditions (Dentice et al., 2011). Indeed, a protective role of DIO3 in cochlear function and integrity has been demonstrated in Dio3$^{-/-}$ mice (Ng et al., 2009). Conversely, the findings that TH signaling promotes cone death provide a beneficial treatment for retinoblastoma, which has properties of a cone precursor tumor (Xu et al., 2009).

In summary, using multiple retinal degeneration mouse models, this Example demonstrates that TH signaling regulates photoreceptor viability in degenerating retinas. Suppressing TH signaling protects cones, whereas stimulating TH signaling has a negative effect on both cones and rods. The regulation of TH signaling on cone survival appears to be independent of its regulatory role in cone opsin expression. The findings of this Example provide insights into cone preservation and specific examples of useful therapeutic interventions.

Example 2

Figure 16:
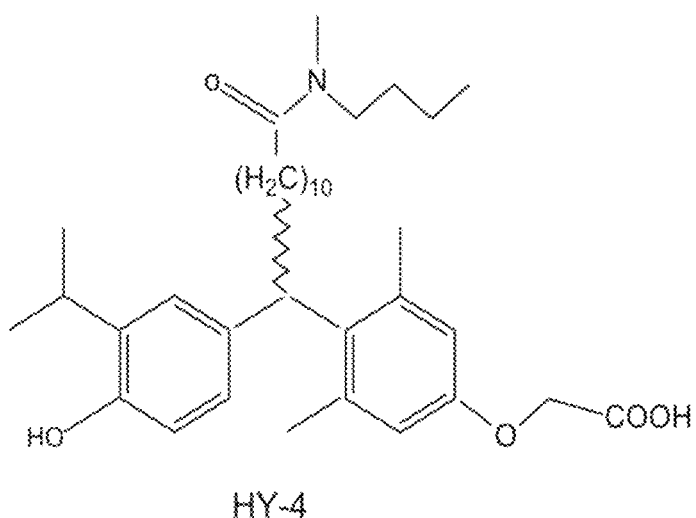
FIG. 16 represents another non-limiting example of a compound that can be used as a TH receptor antagonist in accordance with some embodiments of the presently disclosed inventive concepts; the compound is referred to herein as "HY-4."
Figure 17:
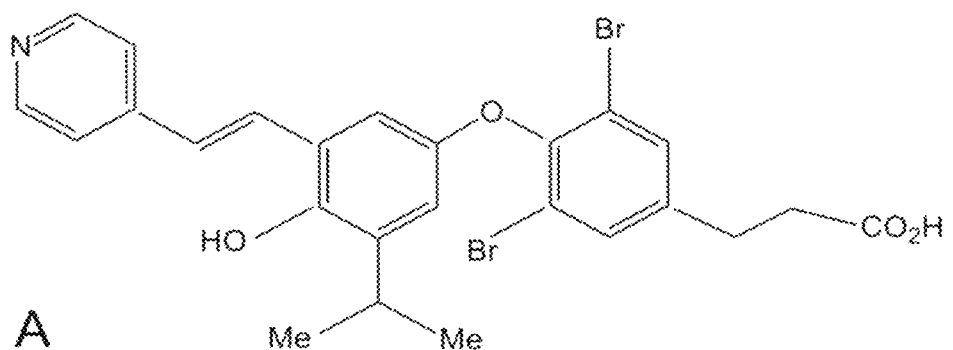
FIG. 17 contains panels A-B that contain additional non-limiting examples of compounds that can be used as TH receptor antagonists in accordance with some embodiments of the presently disclosed inventive concepts.
Figure 17:
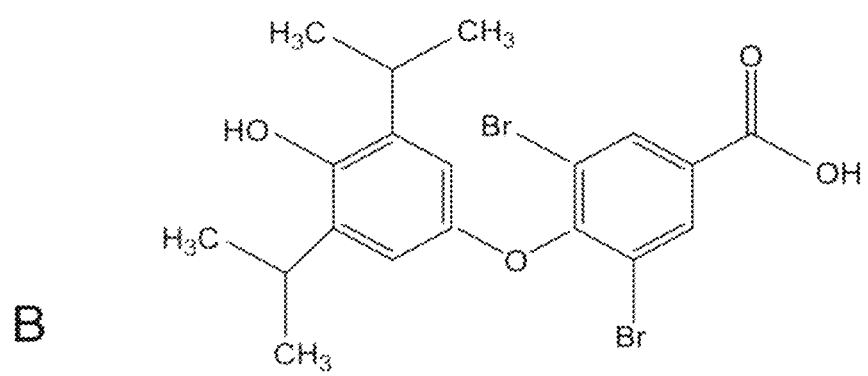
Figure 18:
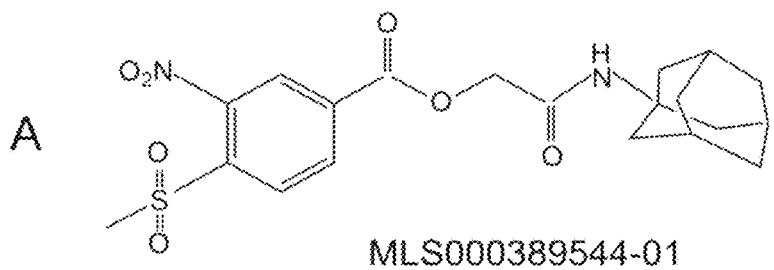
FIG. 18 contains panels A-D that contain non-limiting examples of methylsulfonylnitrobenzoate compounds that can be used as TH receptor antagonists in accordance with alternative embodiments of the presently disclosed inventive concepts.
Figure 18:
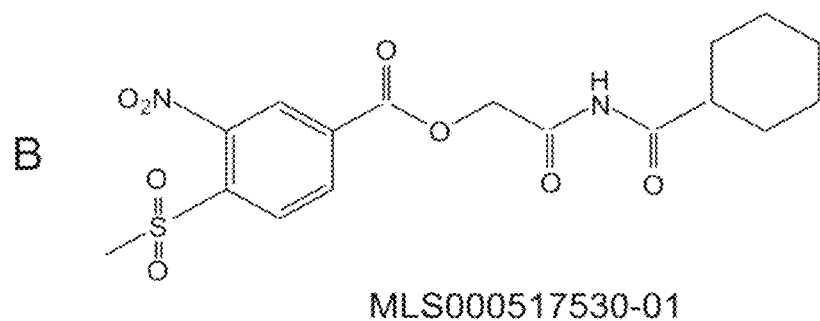
Figure 18:
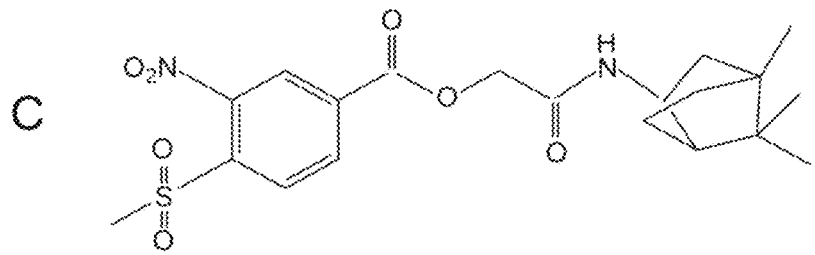
Figure 18:
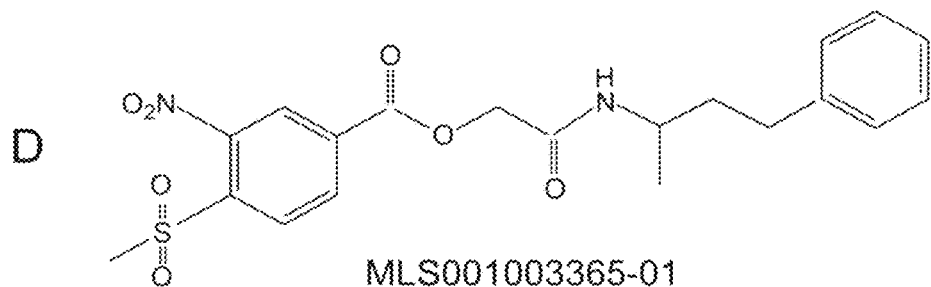
Figure 19:
FIG. 19 contains panels A-E that contain contains non-limiting examples of additional compounds that can be used as TH receptor antagonists in accordance with alternative embodiments of the presently disclosed inventive concepts.
Figure 20:
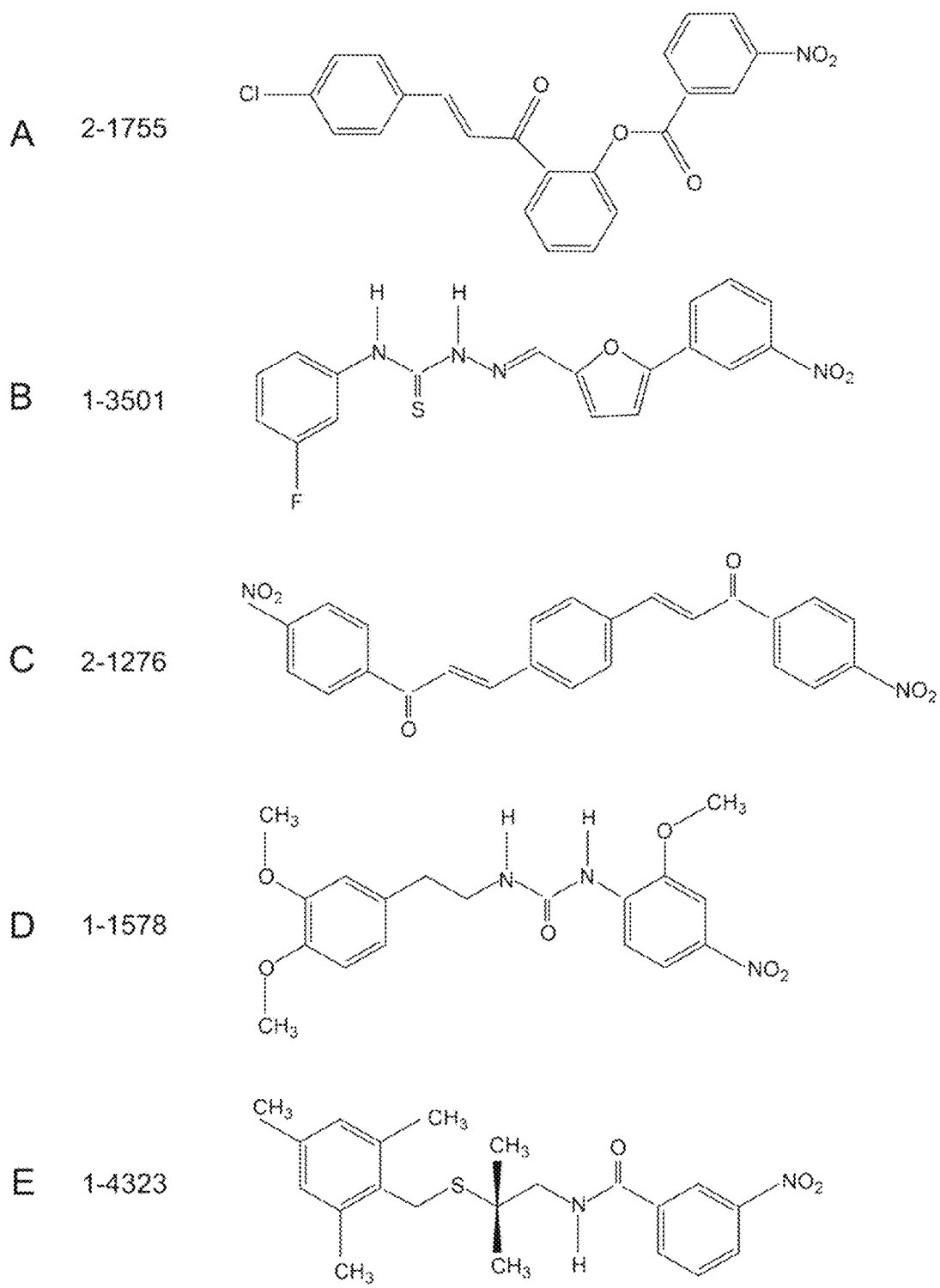
FIG. 20 contains panels A-E that contain additional non-limiting examples of compounds that can be used as TH receptor antagonists in accordance with alternative embodiments of the presently disclosed inventive concepts.
Figure 21:
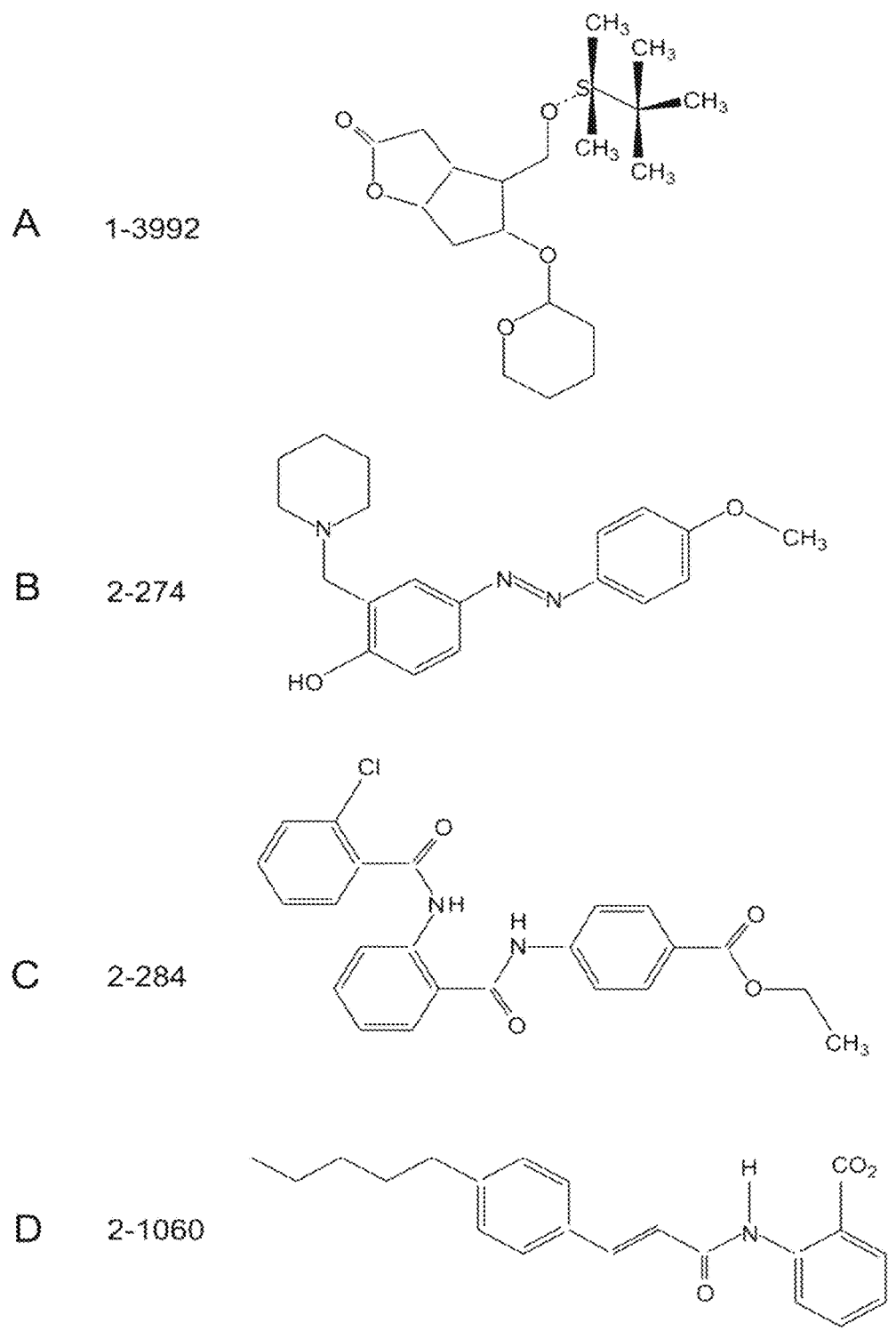
FIG. 21 contains panels A-D that contain additional non-limiting examples of compounds that can be used as TH receptor antagonists in accordance with alternative embodiments of the presently disclosed inventive concepts.
Figure 22:
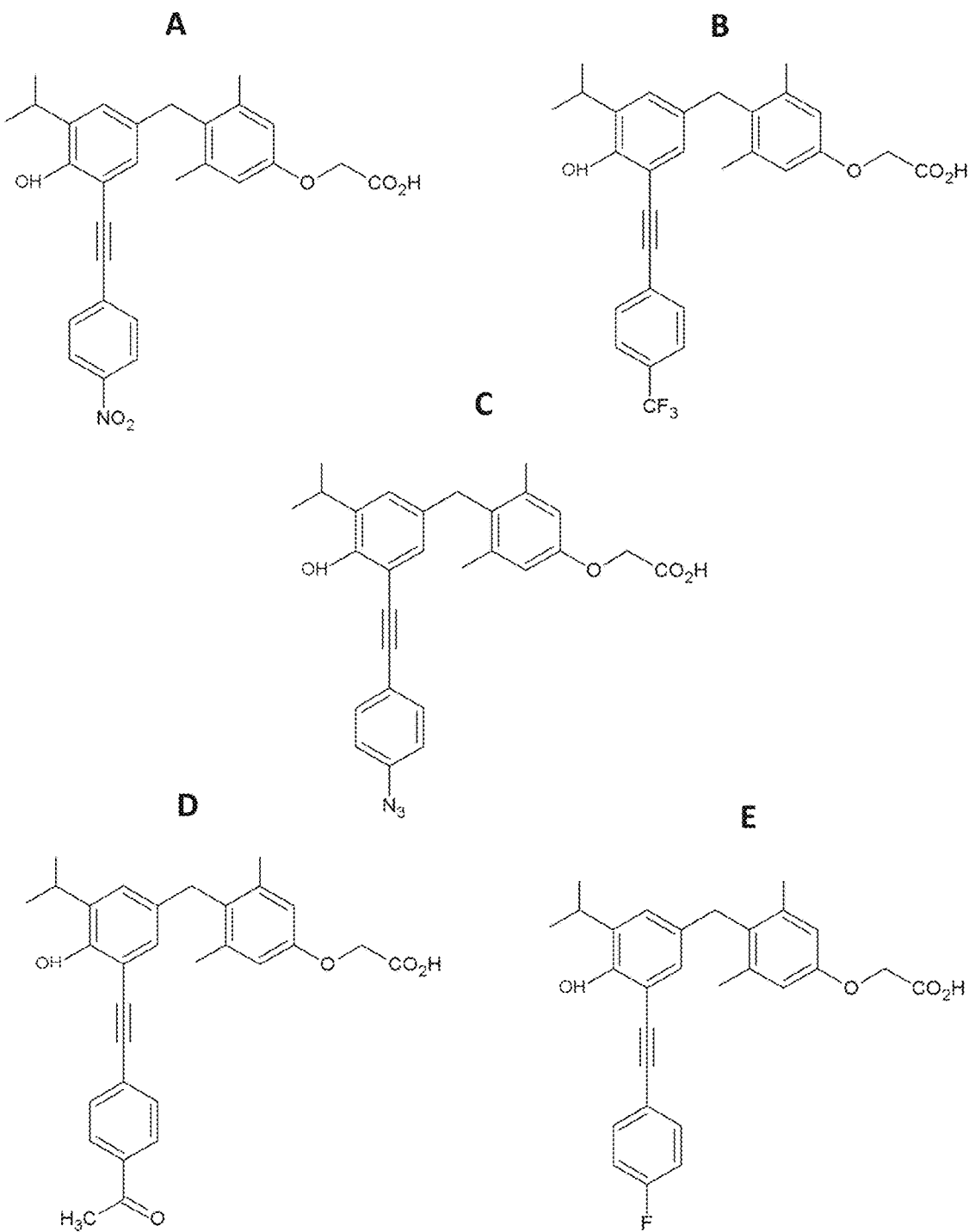
FIG. 22 contains panels A-I that contain non-limiting examples of compounds that are derivatives of the structure shown in FIG. 15 and that can be used as TH receptor antagonists in accordance with alternative embodiments of the presently disclosed inventive concepts.
Figure 22:
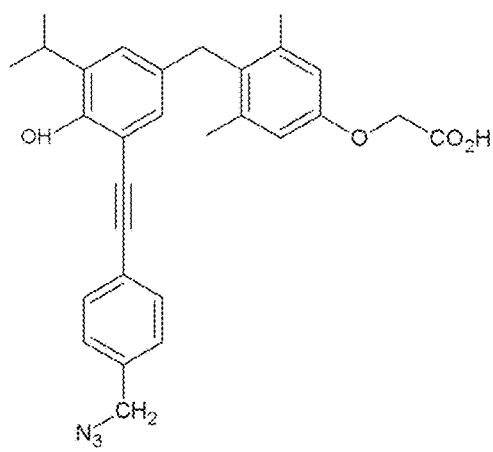
Figure 22:
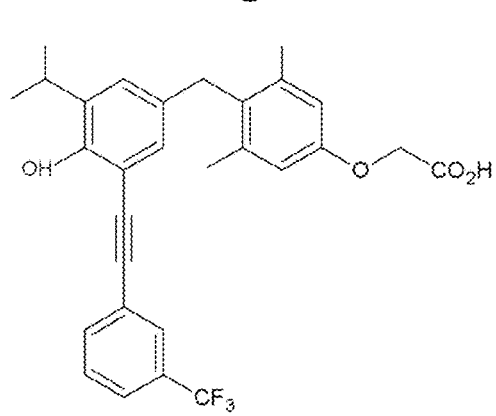
Figure 22:
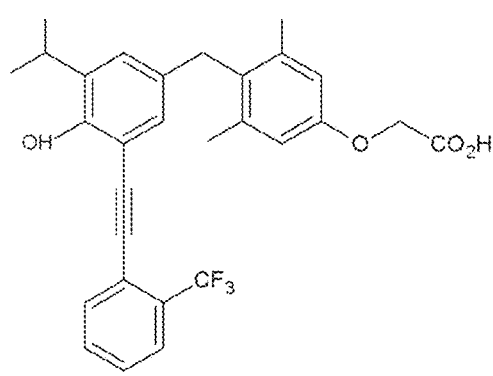
Figure 22:
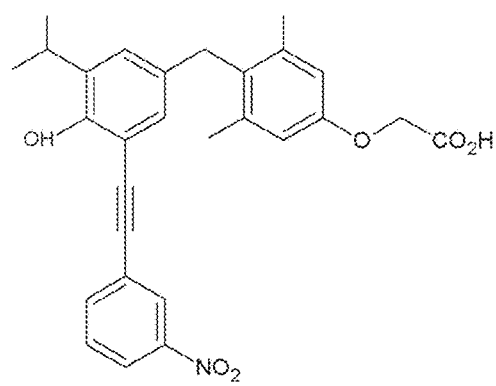
Figure 23:
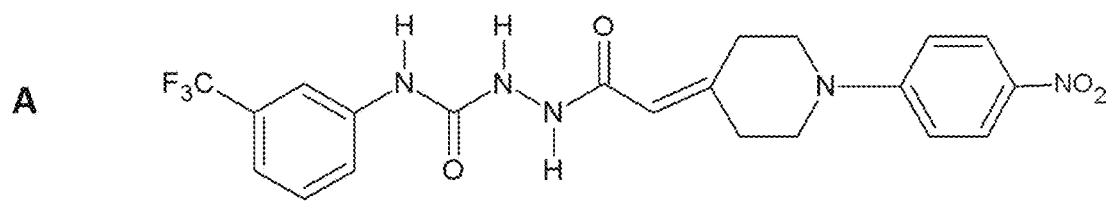
FIG. 23 contains panels A-I that contain non-limiting examples of compounds that are derivatives of the structure shown in FIG. 19A and that can be used as TH receptor antagonists in accordance with alternative embodiments of the presently disclosed inventive concepts.
Figure 23:
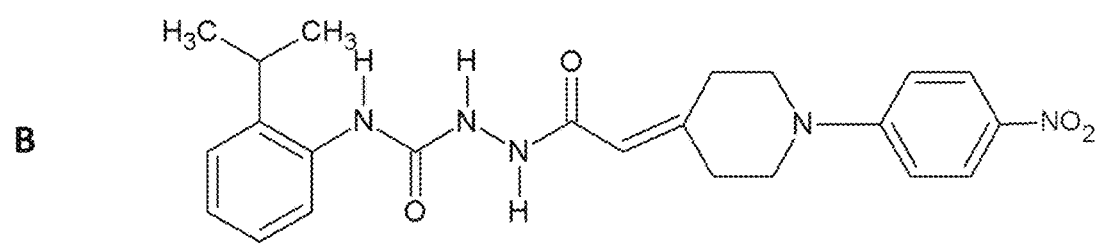
Figure 23:
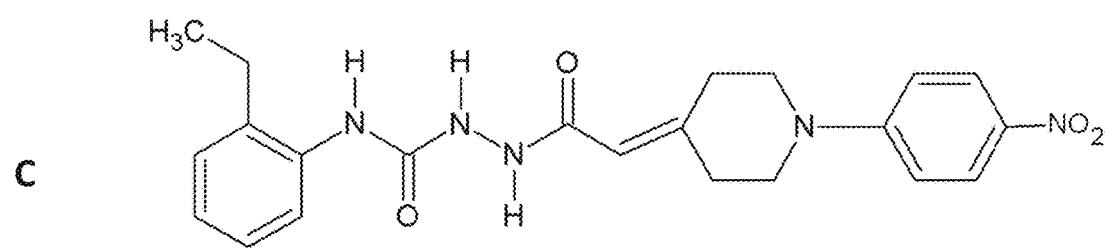
Figure 23:
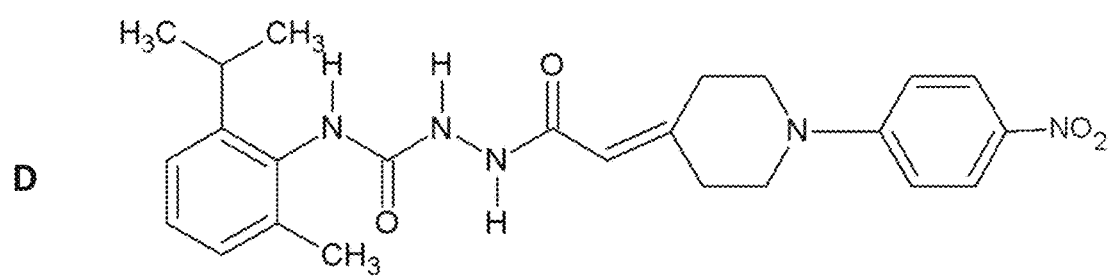
Figure 23:
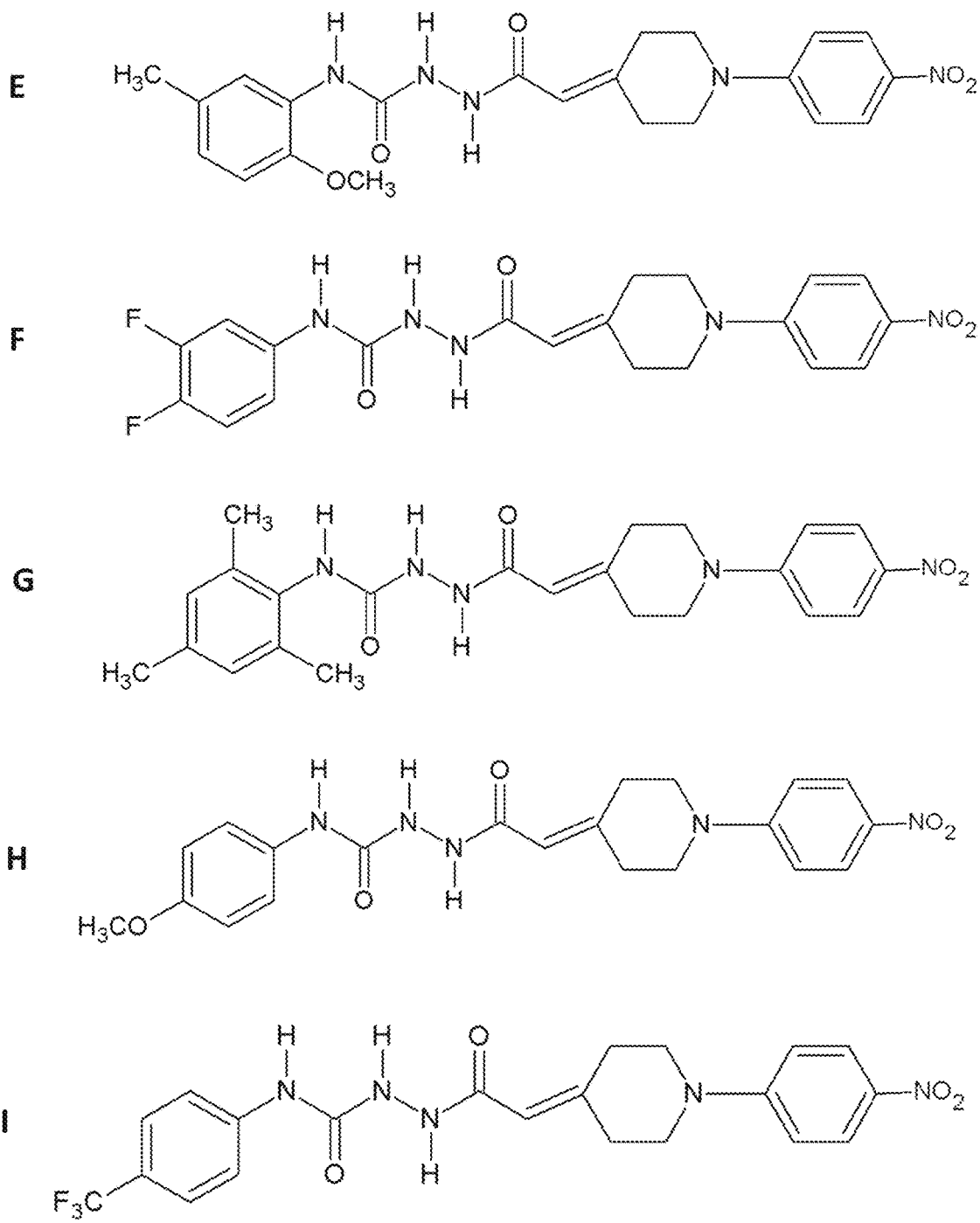

FIGS. 15-24 describe classes of thyroxine derivatives that can be used as TH receptor antagonists in accordance with the presently disclosed inventive concepts. In the compound having the formula shown in FIG. 15 (wherein "p"="para," "m"="meta," and "o"="ortho"), the R group can be selected from the group including, for example, p-NO$_2$ (compound NH-3; FIG. 22A), p-CF$_3$ (compound NH-5; FIG. 22B), p-N$_3$ (compound NH-7; FIG. 22C), p-COCH$_3$ (compound NH-9; FIG. 22D), p-F (compound NH-11; FIG. 22E), p-CH$_2$N$_3$ (compound NH-23; FIG. 22F), m-CF$_3$ (compound NH-17; FIG. 22G), o-CF$_3$ (compound NH-18; FIG. 22H), and m-NO$_2$ (compound NH-19; FIG. 22I) (Nguyen et al., 2005). Compound HY-4 shown in FIG. 16 is discussed in Webb et al. (2002). The compound shown in FIG. 17A is described in further detail in Koehler et al. (2006). Other compounds in this class that may be used in accordance with the presently disclosed inventive concepts are shown in U.S. published patent applications US 2004/0220147, US 2005/0107347, and US 2005/0267206. The compound shown in FIG. 17B is referred to as "DIBRT" and is described in further detail in Baxter et al. (2002).

FIG. 18A-D describes a class of methylsulfonylnitrobenzoates (MSNBs) that can be used as TH receptor antagonists in accordance with the presently disclosed inventive concepts. The compounds having the formulas shown in FIG. 18A-D are described in further detail in Hwang et al. (2011).

FIG. 19A-E, FIG. 20A-E, and FIG. 21A-D describe a diverse class of compounds (referred to as the "1-850 class") that can be used as TH receptor antagonists in accordance with the presently disclosed inventive concepts. Derivatives of compound 1-850 (FIG. 19A) which can be used as TH receptor antagonists in accordance with the presently disclosed inventive concepts include, for example, (1) a compound ("D1") wherein the m-CF$_3$ R group of 1-850 is replaced with o-CH(CH$_3$)$_2$ (FIG. 23B), and (2) a compound ("D4") wherein the m-CF$_3$ R group of 1-850 is replaced with CH(CH$_3$)$_2$ and CH$_3$ in both ortho positions of the aryl group (FIG. 23D). The compounds having the formulas shown in FIG. 19A-E, FIG. 20A-E, and FIG. 21A-D, and the derivatives of compound 1-850 (FIG. 23A-I) are described in further detail in Schapira et al. (2003).

As previously noted, the entire disclosures of each of the publications cited above in regard to FIGS. 15-24 are expressly incorporated by reference herein.

Example 3

Thyroid hormone (TH) signaling regulates cell proliferation, differentiation, and apoptosis. In the retina, TH signaling plays a central role in cone opsin expression and patterning. Example 1 showed that suppressing TH signaling by anti-thyroid treatment preserved cones in mouse models of retinal degeneration. This Example investigates whether the inhibition of thyroid hormone receptors (TRs) affects cone viability in a mouse retinal degeneration model.

FIG. 24 contains the structures of the compounds utilized in this Example; they are referred to herein as NH-3 (FIG. 24A) and 1-850 (FIG. 24B). The chemical name of NH-3 is {4-[4-Hydroxy-3-isopropyl-5-(4-nitrophenylethynyl)benzyl]-3,5-dimethylphenoxy)} acetic Acid. The chemical name of 1-850 is 2-(2-(-(4-Nitrophenyl)-4-piperidinylidene)acetyl-N-(3-(trifluoromethyl)phenyl)-1-hydrazine Carboxamide.

Materials and Methods for Example 3

The cone precursor Weri RB-1 cell line was used to determine the antagonistic activity of the TR antagonists, NH-3 and 1-850. Expression levels of M-opsin and S-opsin in Weri cells following T3 treatment in the presence and absence of TR antagonists were analyzed by quantitative RT-PCR. The cone degeneration mouse model, Rpe65$^{-/-}$, was used to determine whether treatment with TR antagonists protected cones. NH-3, 1-850, or vehicle was delivered to the eye by intravitreal injection at postnatal day 5 (P5), and retinas and eyes were collected on P24. Cone survival was evaluated by examining cone density on retinal whole mounts and retinal sections by immunohistochemical approaches.

Results of Example 3

Figure 25:
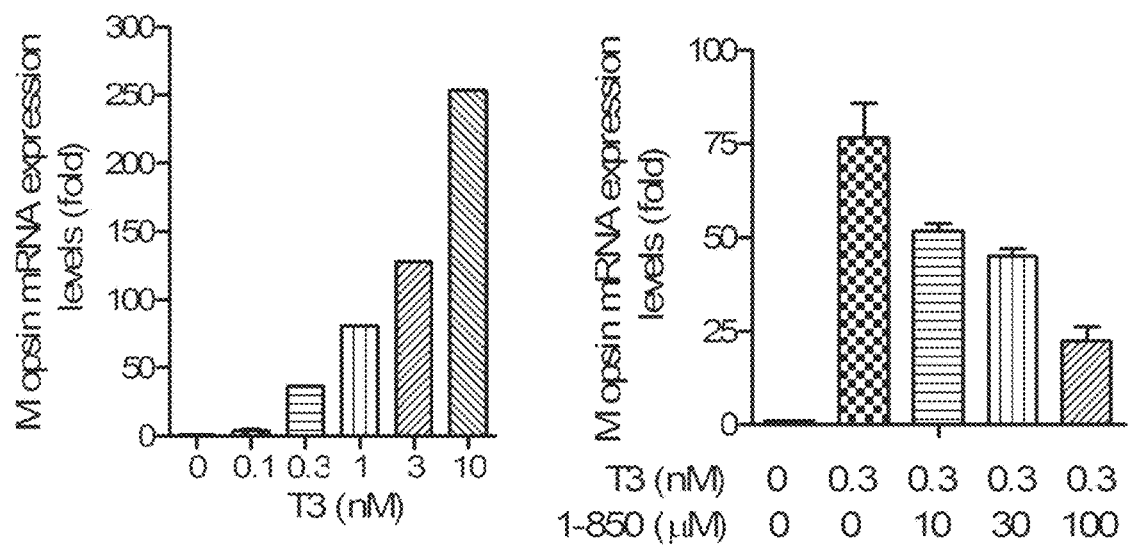
FIG. 25 illustrates that the TR antagonist 1-850 inhibited T3-induced M-opsin expression in photoreceptor Weri cells. Treatment with T3 increased M-opsin expression in Weri cells (left panel), and this effect was inhibited by 1-850 in a dose-dependent pattern (right panel).
Figure 26:
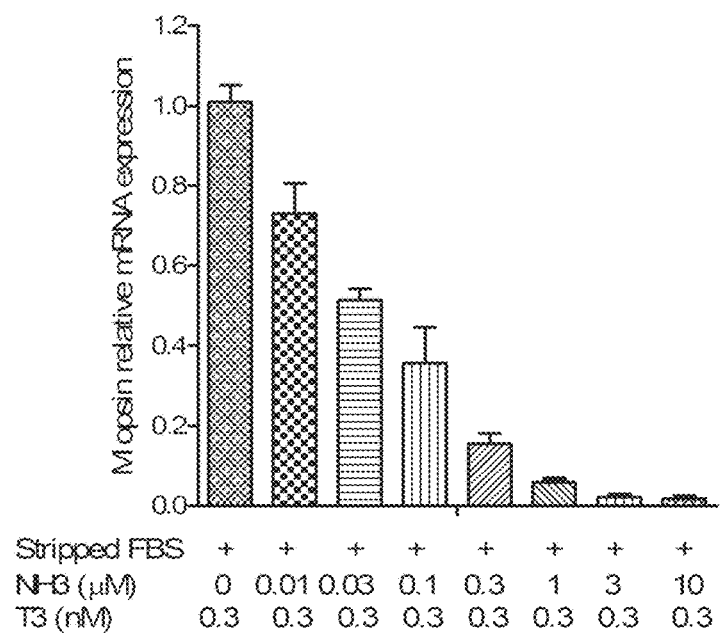
FIG. 26 illustrates that the TR antagonist NH-3 inhibited T3-induced M-opsin expression in photoreceptor Weri cells.

Treatment with T3 increased M-opsin expression (FIG. 25, left panel) and decreased S-opsin expression in Weri cells. The effects of T3 treatment were inhibited by NH-3 and 1-850 in a dose-dependent pattern (FIG. 25, right panel, and FIG. 26, respectively).

Figure 27:
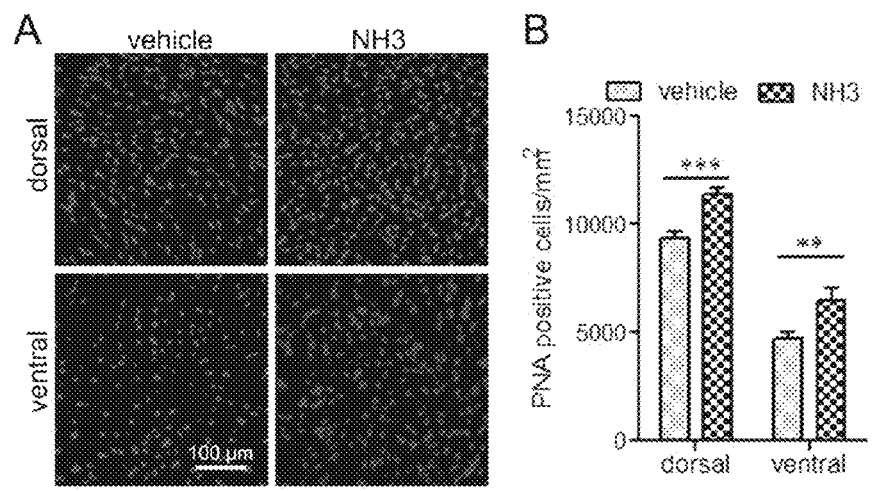
FIG. 27 illustrates that intravitreal delivery of the TR antagonist NH-3 protected cones in Rpe65$^{-/-}$ mice. Mice were injected intravitreally with 1.0 μl of 5 mM NH-3 or vehicle at postnatal day 5 (P5). Retinas were collected at P24, and retinal whole mounts were prepared for peanut agglutinin (PNA) staining. Shown are representative confocal images (A) and correlating quantitative analysis (B). Confocal images were taken from the middle part of the dorsal and ventral retinas. Data are represented as mean±SEM from 3-4 assays using eyes prepared from 6-8 mice. Unpaired Student t test was used to evaluate the significances of differences between NH-3-treated and vehicle-treated mice (** P<0.01).
Figure 28:
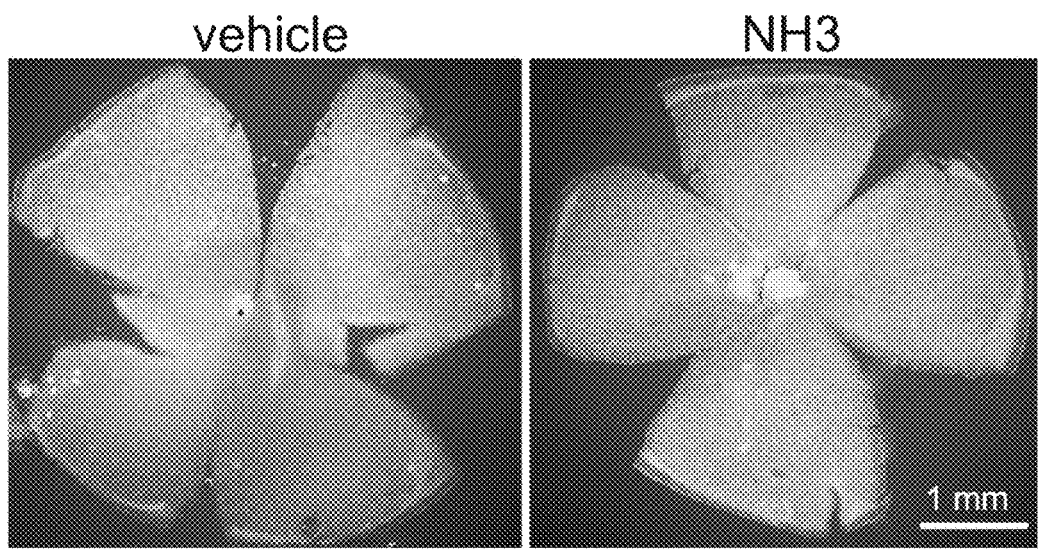
FIG. 28 contains photomicrographs that illustrate that intravitreal delivery of the TR antagonist NH-3 reduced cone death in Rpe65$^{-/-}$ mice.
Figure 29:
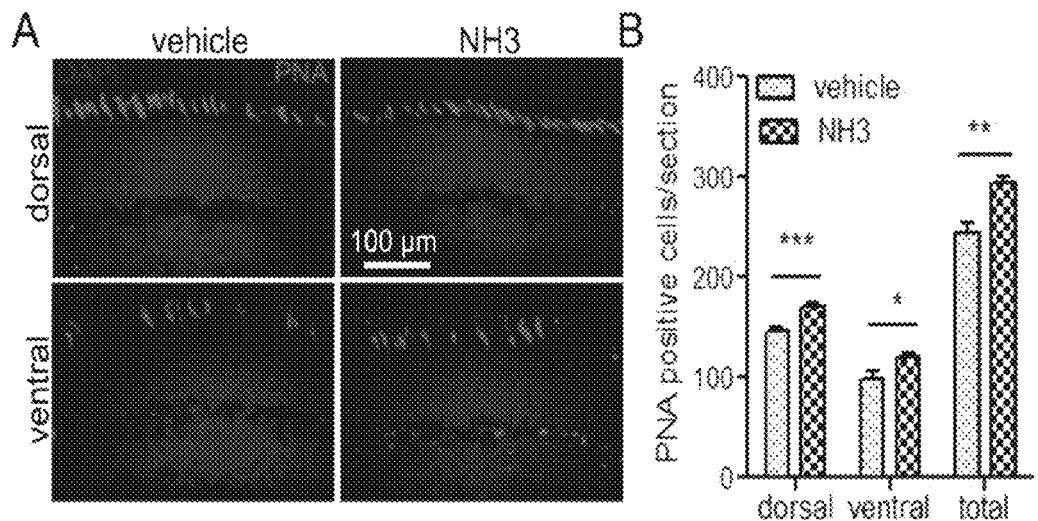
FIG. 29 illustrates that the TR antagonist NH-3 protected cones in Rpe65$^{-/-}$ mice. Mice were injected intravitreally with 1.0 μl of 5 mM NH-3 or vehicle at P5. Eyes were collected at P24, and retina sections were prepared for PNA staining. Shown are representative confocal images (A) and correlating quantitative analysis (B). Confocal images were taken from the middle part of the dorsal and ventral retinas, and PNA positive cones were counted on sections passing through the optical nerve. Data are represented as mean±SEM from 3-4 assays using eyes prepared from 6-8 mice. Unpaired Student t test was used to evaluate the significances of differences between NH-3-treated and vehicle-treated mice (* P<0.05;  P<0.01; * P<0.001).
Figure 30:
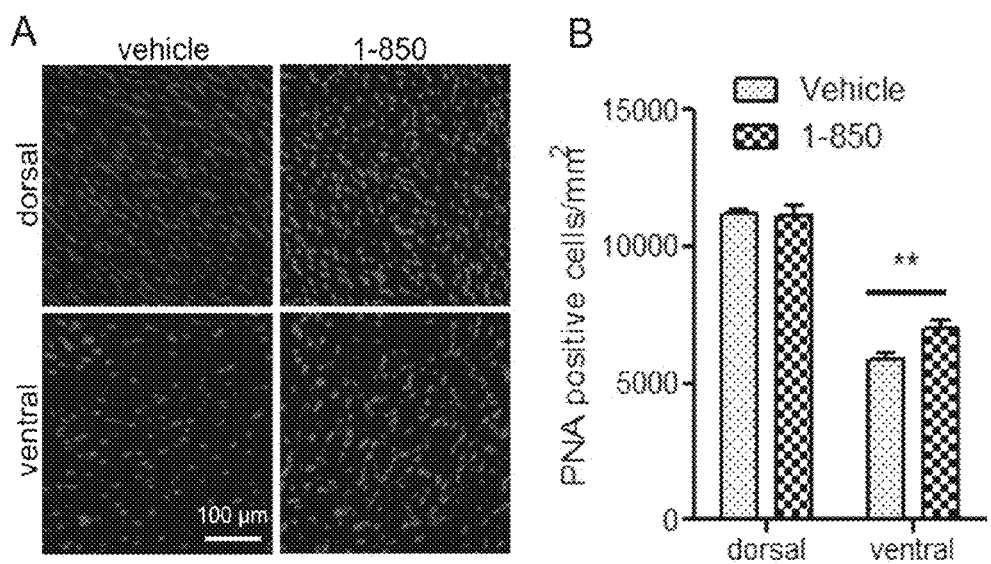
FIG. 30 illustrates that the TR antagonist 1-850 protected cones in Rpe65$^{-/-}$ mice. Mice were injected intravitreally with 1.0 μl of 10 mM 1-850 or vehicle at P5. Retinas were collected at P24, and retinal whole mounts were prepared for PNA staining. Shown are representative confocal images (A) and correlating quantitative analysis (B). Confocal images were taken on the middle part of the dorsal and ventral retinas. Data are represented as mean±SEM from 3-4 assays using eyes prepared from 6-8 mice. Unpaired Student t test was used to evaluate the significances of differences between 1-850-treated and vehicle-treated mice (** P<0.01).
Figure 31:
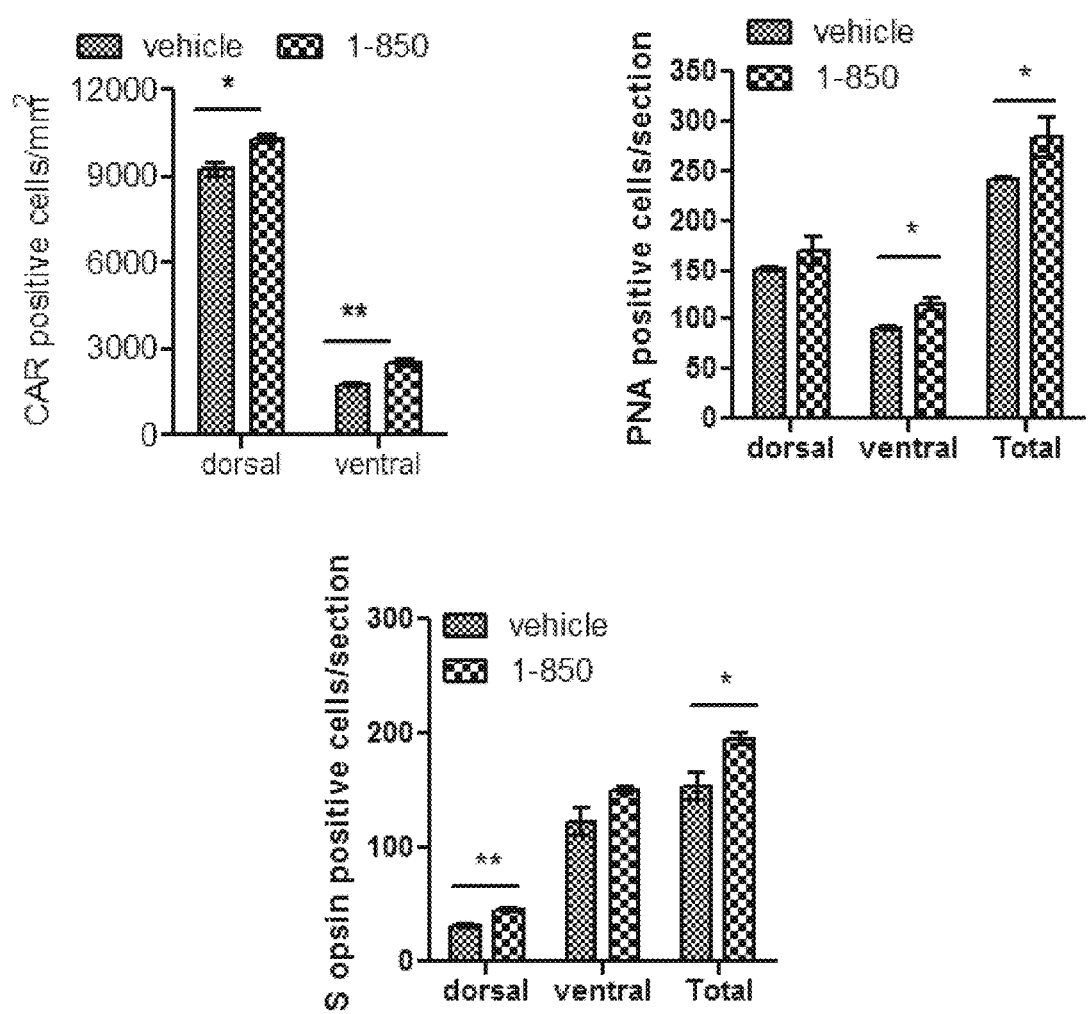
FIG. 31 illustrates that intravitreal delivery of the TR antagonist 1-850 reduced cone death in Rpe65-/- mice. Mice were injected intravitreally with 1.0 μl of 10 mM 1-850 or vehicle at P5. Retinas were collected at P24, and retinal whole mounts and sections were prepared for CAR, PNA, and S opsin staining. Shown are quantitative analysis of cone density analyzed by CAR staining on retinal whole mounts, and by PNA and S-opsin staining on retinal sections. Data are represented as mean±SEM from 3-4 assays using eyes prepared from 6-8 mice. Unpaired Student t test was used to evaluate the significances of differences between 1-850-treated and vehicle-treated mice (* P<0.05; ** P<0.01).

The effects of these two TR antagonists on cone degeneration was then investigated in Rpe65$^{-/-}$ mice, using the methods disclosed in Example 1. FIGS. 27, 28, and 29 illustrate that intravitreal injection of the TR antagonist NH-3 protected cones in Rpe65$^{-/-}$ mice, while FIGS. 30 and 31 illustrate that intravitreal injection of the TR antagonist 1-850 protected cones in Rpe65$^{-/-}$ mice. Cone density in Rpe65$^{-/-}$ mice increased by about 35% following NH-3 and 1-850 treatment.

In summary, this Example demonstrates that treatment with TR antagonists ocularly improved cone survival in Rpe65$^{-/-}$ mice. These findings demonstrate that inhibition of TR signaling locally in the retina represents a novel strategy for retinal degeneration management.

Although the presently described inventive concepts have been described in detail, it should be understood that various changes, substitutions and alterations can be made herein without departing from the spirit and scope of the presently described inventive concepts as defined in the appended claims. Moreover, the scope of the presently described inventive concepts is not intended to be limited to the particular examples and embodiments of the process, items of manufacture, compositions of matter, means, methods and steps described in the specification or in the appended claims. As one of ordinary skill in the art will readily appreciate from the present disclosure, processes, items of manufacture, compositions of matter, means, methods, or steps, presently existing or later to be developed that perform substantially the same function or achieve substantially the same result as the corresponding examples and embodiments described herein may be utilized according to the presently described inventive concept. Accordingly, the appended claims are intended to include within their scope such processes, items of manufacture, compositions of matter, means, methods, or steps.

REFERENCES

The following references, to the extent that they provide exemplary procedural or other details supplementary to those set forth herein, are specifically incorporated herein by reference.

Applebury et al. (2007) *Dev Dyn*, 236(5): 1203-1212.
Baxter et al. (2002) *Endocrinology*, 143(2): 517-24.
Cheng et al. (2010) *Endocr Rev*, 31(2):139-170.
Chiloeches et al. (2008) *Mol Endocrinol*, 22(11):2466-2480.
Dentice et al. (2011) *J Endocrinol*, 209(3):273-282.
Ding et al. (2009) *Hum Mol Genet*, 18(24):4770-4780.
Glaschke et al. (2010) *Invest Ophthalmol Vis Sci*, 51(3): 1719-1727.
Hiroi et al. (2006) *Proc Natl Acad Sci USA*, 103(88):14104-14109.
Hwang et al. (2011) *J Biol Chem*, 286(14): 11895-908.
Koehler et al. (2006) *J Med Chem*, 49(23): 6635-7.
Komeima et al. (2006) *Proc Natl Acad Sci*, 103(30): 11300-11305.
Lu et al. (2009) *Endocrinology*, 150(3): 1536-1544.
Ma et al. (2013) *Hum Mol Genet*, 22(19):3906-3919.
Mihara et al. (1999) *J Clin Endocrinol Metab*, 84(4):1378-1385.
Ng et al. (2001) *Nat Genet*, 27(1):94-98.
Ng et al. (2009) *Endocrinology*, 150(4): 1952-1960.
Ng et al. (2009) *Neuroreport*, 20(6):627-631.
Nguyen et al. (2005) *J Am Chem Soc*. 127(13):4599-608.
Redmond et al. (1998) *Nat Genet*, 20(4):344-351.
Sar et al. (2011) *PLoS One*, 6(6):e20861.
Schapira et al. (2003) *Proc Natl Acad Sci USA*, 100(12): 7354-9.
Webb et al. (2002) *J Steroid Biochem Mol Biol*, 83(1-5): 59-73.
Weiss et al. (2012) *Ophthalmic Genet*, 33(4):187-195.
Xu et al. (2009) *Cell*, 137(6):1018-1031.
Xu et al. (2011) *Invest Ophthalmol Vis Sci*, 52(6):3557-3566.
Xu et al. (2012) *Invest Ophthalmol Vis Sci*, 53(3): 1117-1129.
Yamada-Okabe et al. (2003) *Eur J Biochem*, 270(14): 3064-3073.
Yang et al. (1999) *J Neurosci*, 19(14):5889-5897.

What is claimed is:

1. A method of enhancing cone photoreceptor survival in a subject having a pathologic ocular condition, the method comprising the step of:
administering to the subject a pharmaceutical composition comprising at least one antagonist of nuclear thyroid hormone receptor (TR), wherein the pharmaceutical composition is administered in an amount effective to inhibit and/or reduce nuclear thyroid hormone signaling in the retina of at least one eye of the subject, thereby enhancing cone photoreceptor survival in the subject, and wherein the at least one antagonist of nuclear thyroid hormone receptor is represented by Formula (I):

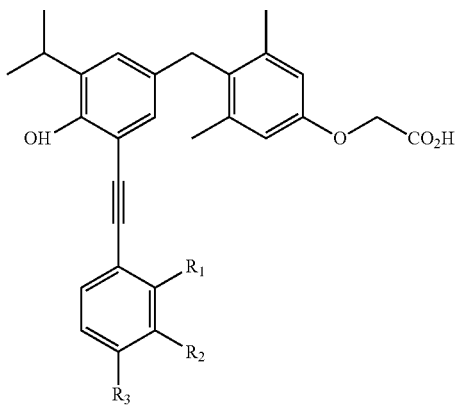

Formula (I)

wherein:

$R_1$ is $CF_3$, and $R_2$ and $R_3$ are H;

$R_2$ is $CF_3$ or $NO_2$, and $R_1$ and $R_3$ are H; or $R_3$ is $CF_3$, $NO_2$, $N_3$, $COCH_3$, F, or $CH_2N_3$, and $R_1$ and $R_3$ are H; and wherein the pathologic ocular condition is at least one of age-related macular degeneration, Stargardt disease, retinitis pigmentosa, Usher syndrome, Leber's congenital amaurosis, achromatopsia, a rod-cone dystrophy, a cone-rod dystrophy, Bardet-Biedel syndrome, juvenile retinoschisis, choroideremia, and diabetic retinopathy.

2. The method of claim 1, wherein the pharmaceutical composition is administered topically to or by injection into at least one eye of the subject.

3. The method of claim 1, wherein the subject is a mammal.

4. The method of claim 1, wherein the at least one antagonist is an antagonist of nuclear thyroid hormone receptor TRβ2.

5. The method of claim 1, wherein the pharmaceutical composition further comprises at least one delivery agent that assists in delivery of the at least one antagonist to the at least one eye of the subject.

* * * * *

UNITED STATES PATENT AND TRADEMARK OFFICE
CERTIFICATE OF CORRECTION

PATENT NO. : 10,258,613 B2
APPLICATION NO. : 15/115819
DATED : April 16, 2019
INVENTOR(S) : Xi-Qin Ding and Hongwei Ma It is certified that error appears in the above-identified patent and that said Letters Patent is hereby corrected as shown below:

In the Specification

Column 2, Line 52: Delete "5-opsin" and replace with -- S-opsin --

Column 3, Line 10: Delete "GNAT," and replace with -- GNAT2 --

Column 3, Line 10: Delete "5-opsin" and replace with -- S-opsin --

Column 3, Line 18: Delete "5-opsin" and replace with -- S-opsin --

Column 3, Line 38: Delete "d-=SEM" and replace with -- ± SEM --

Column 4, Line 8: Delete "5-opsin" and replace with -- S-opsin --

Signed and Sealed this
Twenty-first Day of May, 2019

Andrei Iancu
*Director of the United States Patent and Trademark Office*